US009925048B2

(12) United States Patent
Winslow et al.

(10) Patent No.: US 9,925,048 B2
(45) Date of Patent: Mar. 27, 2018

(54) MODULAR GLENOID BASE PLATE WITH AUGMENTS

(71) Applicant: Biomet Manufacturing, LLC, Warsaw, IN (US)

(72) Inventors: Nathan A. Winslow, Warsaw, IN (US); Andrew Matthew Telka, Warsaw, IN (US); Aaron Smits, Fort Wayne, IN (US); John M. McDaniel, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 15/434,244

(22) Filed: Feb. 16, 2017

(65) Prior Publication Data

US 2017/0224492 A1   Aug. 10, 2017

Related U.S. Application Data

(63) Continuation of application No. 14/028,930, filed on Sep. 17, 2013, now Pat. No. 9,668,873.

(60) Provisional application No. 61/775,119, filed on Mar. 8, 2013.

(51) Int. Cl.
*A61F 2/40*    (2006.01)
*A61F 2/30*    (2006.01)

(52) U.S. Cl.
CPC ........ *A61F 2/30734* (2013.01); *A61F 2/4081* (2013.01); *A61F 2/4003* (2013.01); *A61F 2/4014* (2013.01); *A61F 2002/3085* (2013.01); *A61F 2002/30433* (2013.01); *A61F 2002/30576* (2013.01); *A61F 2002/30736* (2013.01); *A61F 2002/30738* (2013.01); *A61F 2002/30787* (2013.01); *A61F 2002/30948* (2013.01); *A61F 2002/4085* (2013.01)

(58) Field of Classification Search
CPC .................................................... A61F 2/4081
See application file for complete search history.

(56) References Cited

U.S. PATENT DOCUMENTS

| 4,524,467 | A  | 6/1985  | Decarlo, Jr. et al. |
| 6,783,549 | B1 | 8/2004  | Stone et al. |
| 9,668,873 | B2 | 6/2017  | Winslow et al. |
| 2007/0173945 | A1 | 7/2007  | Wiley et al. |
| 2010/0274359 | A1 | 10/2010 | Brunnarius et al. |
| 2011/0144756 | A1 | 6/2011  | Bickley et al. |
| 2012/0130499 | A1 | 5/2012  | Long |
| 2013/0110470 | A1 | 5/2013  | Vanasse et al. |

(Continued)

FOREIGN PATENT DOCUMENTS

| WO | WO-2012141790 A1 | 10/2012 |
| WO | WO 2014138424 A1 | 9/2014 |
| WO | WO-PCT A1 | 9/2014 |
|    | US2014021281 | |

OTHER PUBLICATIONS

U.S. Appl. No. 14/028,930, filed Sep. 17, 2013, Modular Glenoid Base Plate With Augments.

(Continued)

*Primary Examiner* — David Isabella
*Assistant Examiner* — Javier Blanco
(74) *Attorney, Agent, or Firm* — Schwegman Lundberg & Woessner, P.A.

(57) ABSTRACT

An implant assembly comprising a bone augment and an articulating member. The bone augment includes a bone-engaging surface and a coupling surface. The articulating member is configured to couple with the bone augment.

6 Claims, 18 Drawing Sheets

(56) References Cited

U.S. PATENT DOCUMENTS

2013/0150972 A1 6/2013 Iannotti et al.
2014/0257499 A1 9/2014 Winslow et al.

OTHER PUBLICATIONS

"U.S. Appl. No. 14/028,930, Examiner Interview Summary dated Oct. 29, 2015", 3 pgs.
"U.S. Appl. No. 14/028,930, Final Office Action dated Feb. 8, 2014", 14 pgs.
"U.S. Appl. No. 14/028,930, Non Final Office Action dated Jul. 28, 2015", 12 pgs.
"U.S. Appl. No. 14/028,930, Notice of Allowance dated Feb. 2, 2017", 15 pgs.
"U.S. Appl. No. 14/028,930, Response filed May 26, 2015 to Restriction Requirement dated Feb. 23, 2015", 10 pgs.
"U.S. Appl. No. 14/028,930, Response filed Jun. 7, 2016 to Final Office Action dated Feb. 8, 2016", 14 pgs.
"U.S. Appl. No. 14/028,930, Response filed Oct. 28, 2015 to Non Final Office Action dated Jul. 28, 2015", 15 pgs.
"U.S. Appl. No. 14/028,930, Restriction Requirement dated Feb. 23, 2015", 8 pgs.
"International Application Serial No. PCT/US2014/021281, International Preliminary Report on Patentability dated Sep. 17, 2015", 8 pgs.
"International Application Serial No. PCT/US2014/021281, International Search Report dated May 27, 2014", 4 pgs.
"International Application Serial No. PCT/US2014/021281, Written Opinion dated May 27, 2014".
"European Application Serial No. 14712508.2, Communication Pursuant to Article 94(3) EPC dated Jul. 4, 2017", 4 pgs.
"Australian Application Serial No. 2014225636, First Examination Report dated Aug. 21, 2017", 5 pgs.
"European Application Serial No. 14712508.2, Response filed Nov. 13, 2017 to Communication Pursuant to Article 94(3) EPC dated Jul. 4, 2017", 4 pgs.

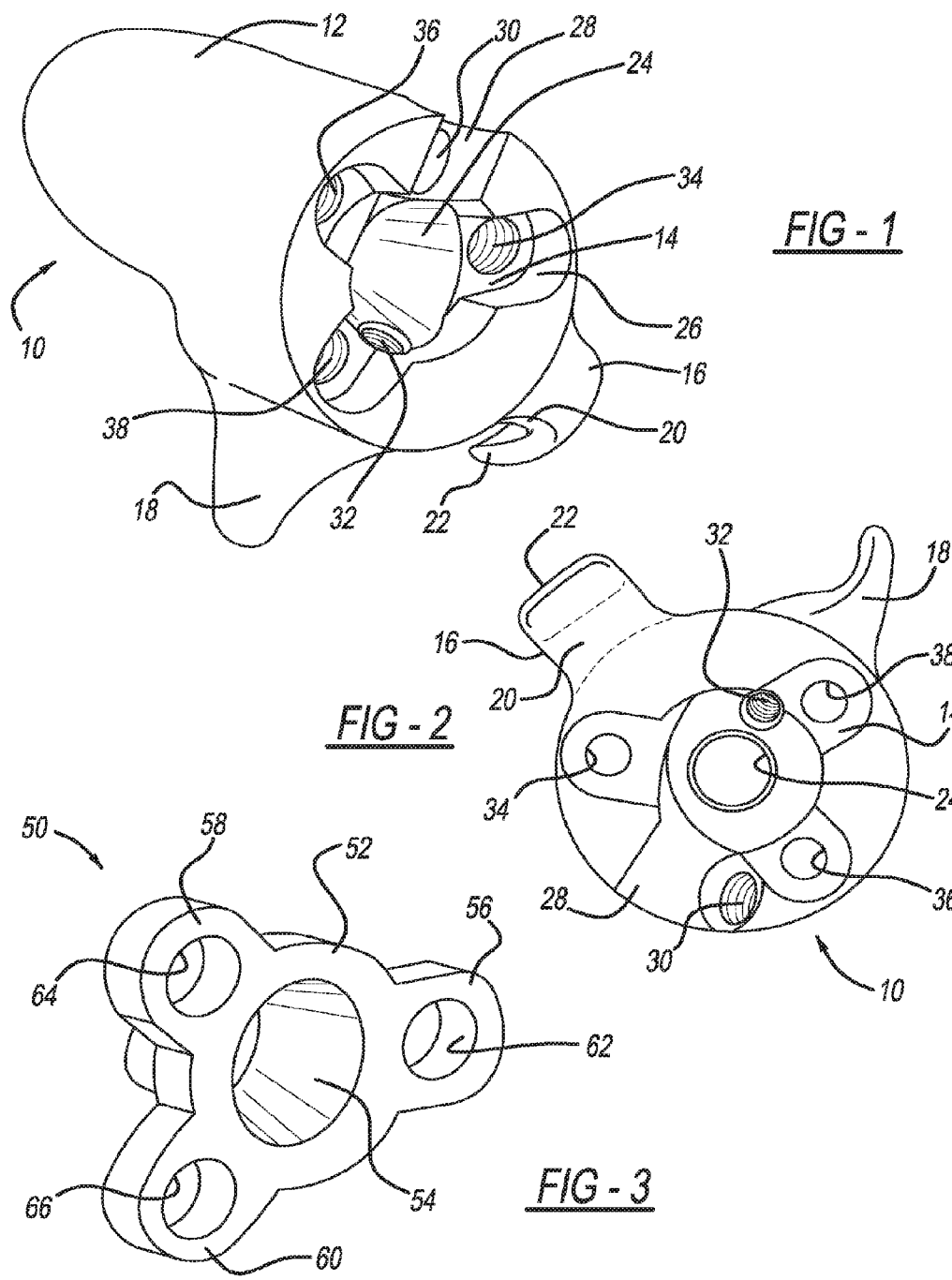

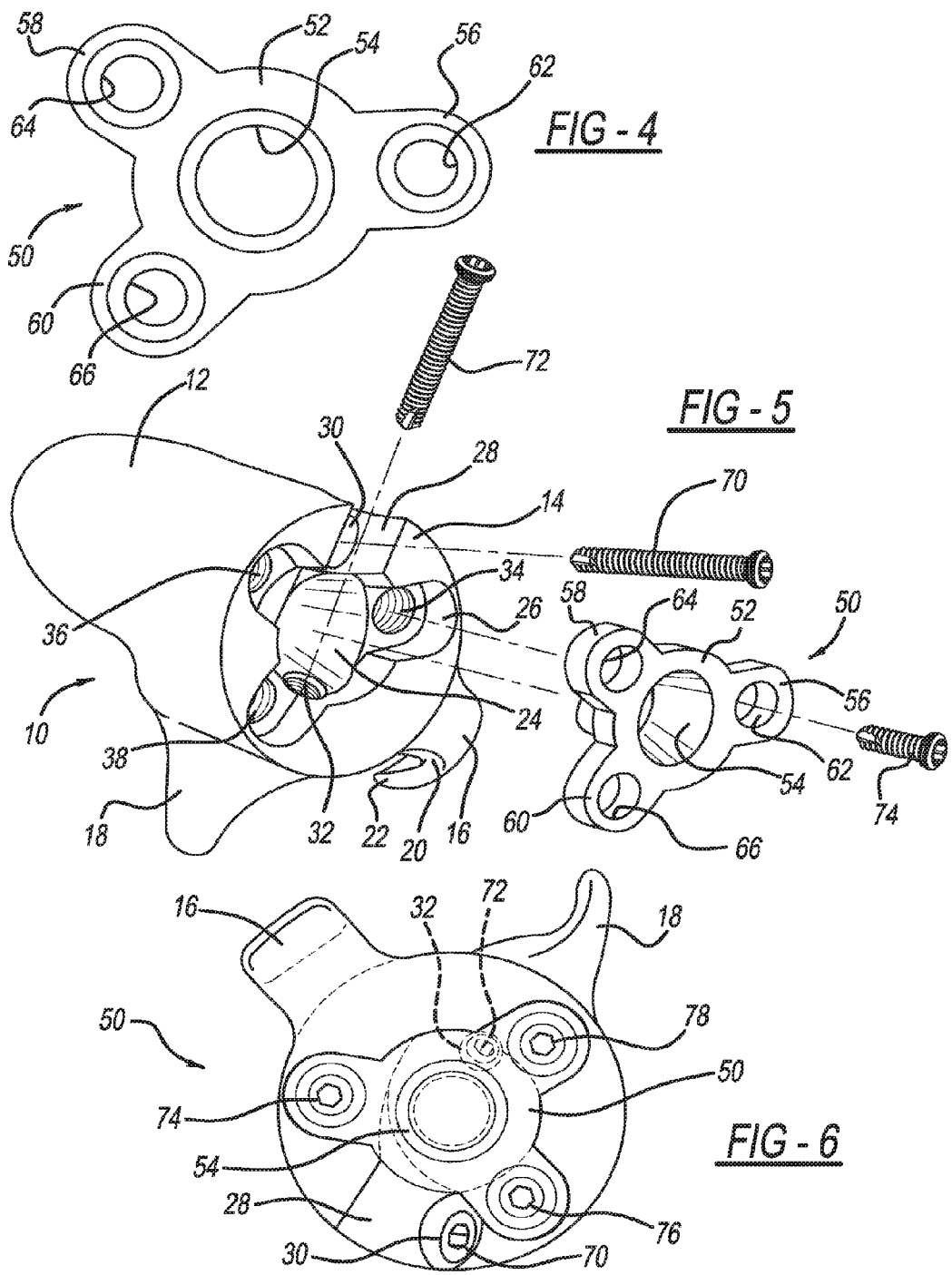

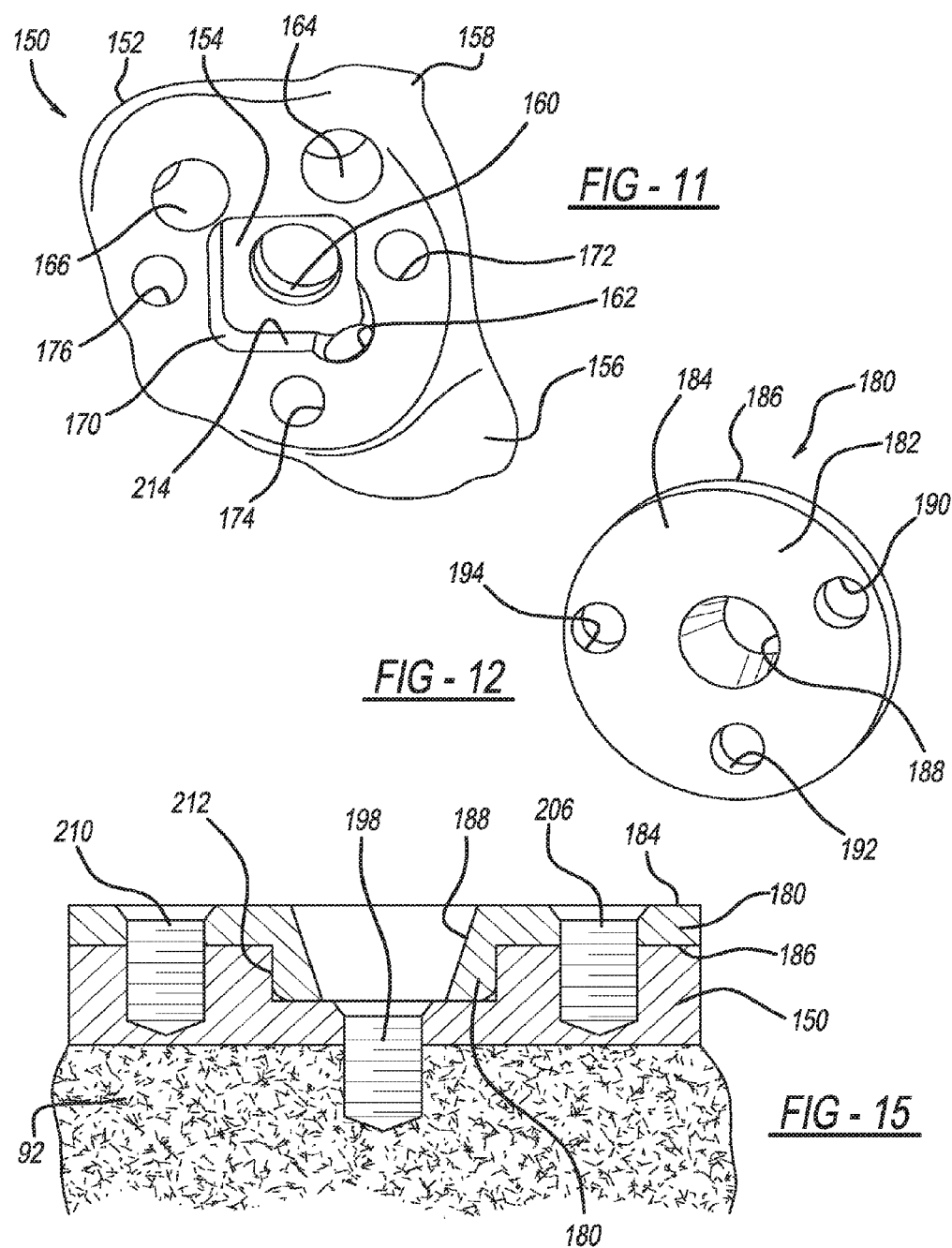

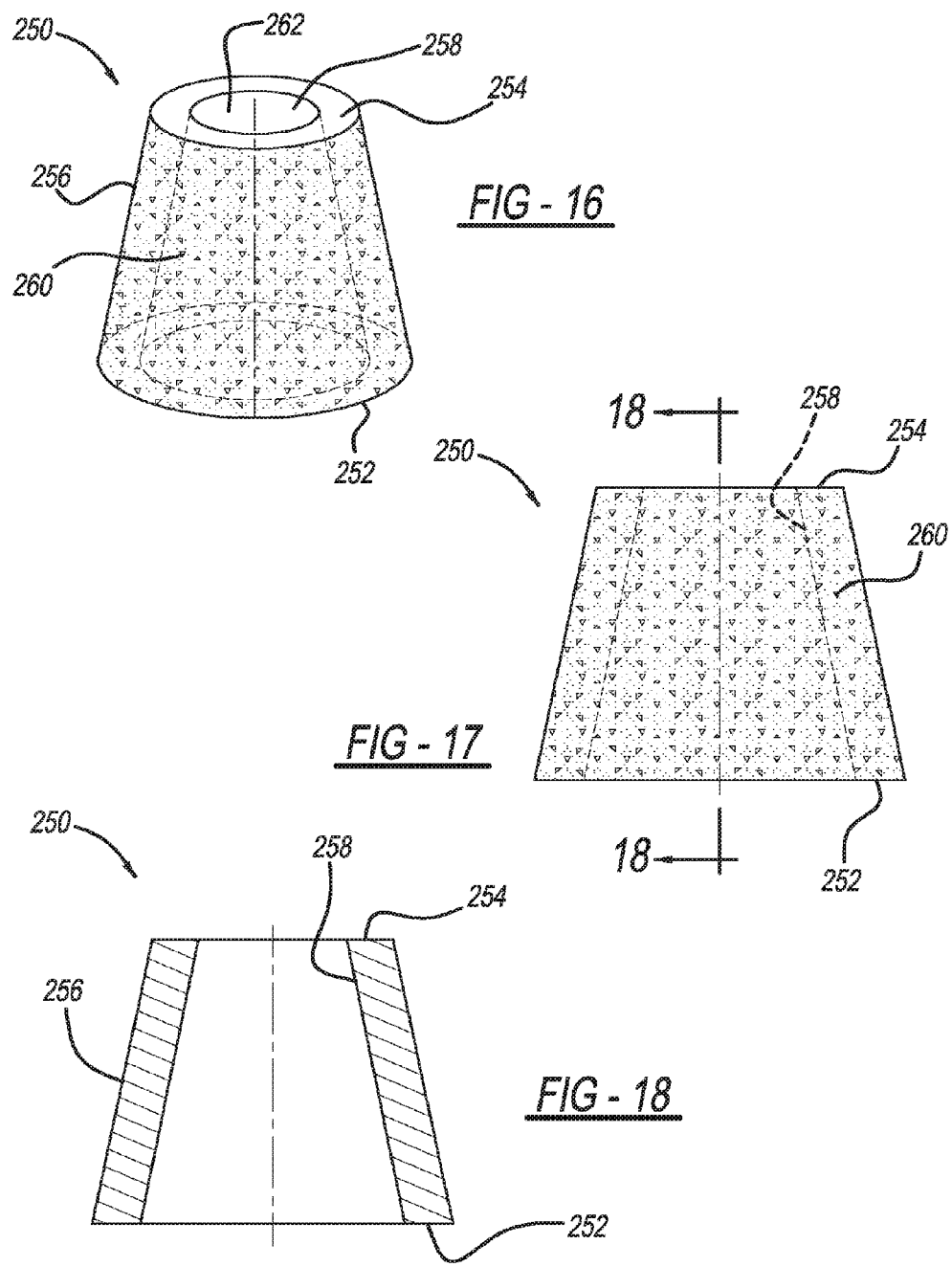

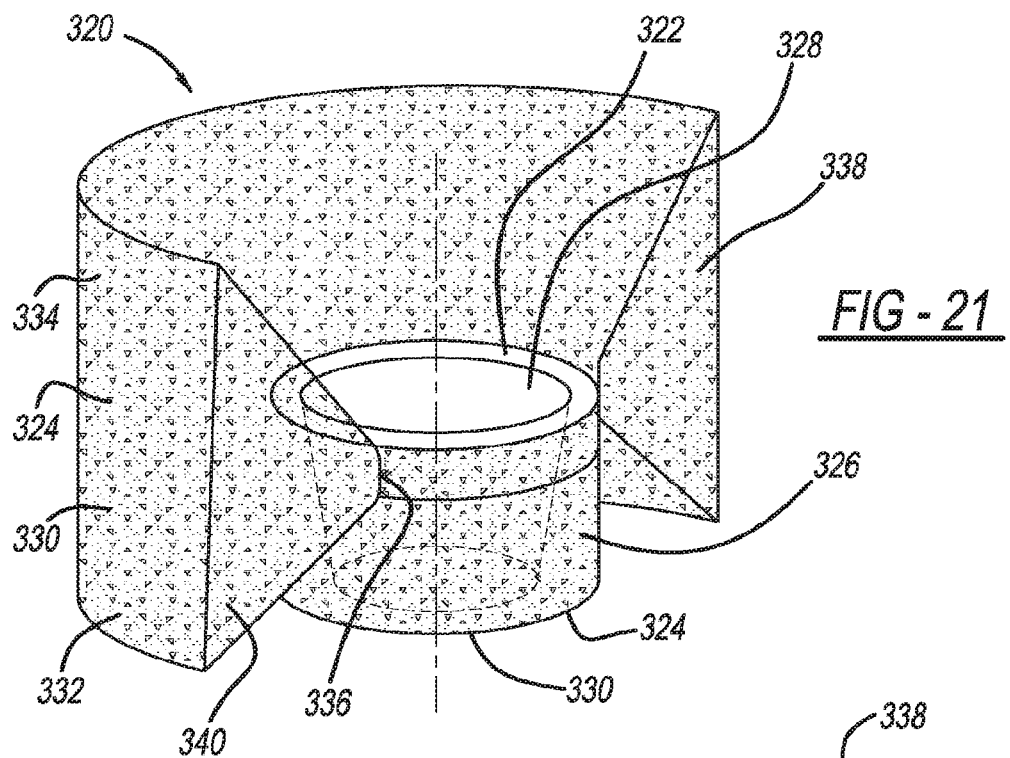
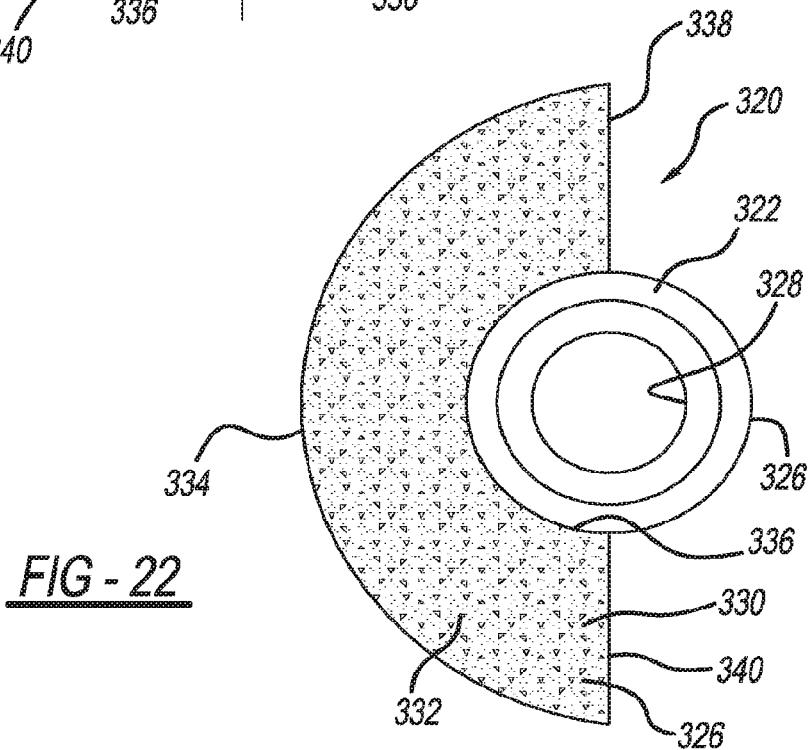

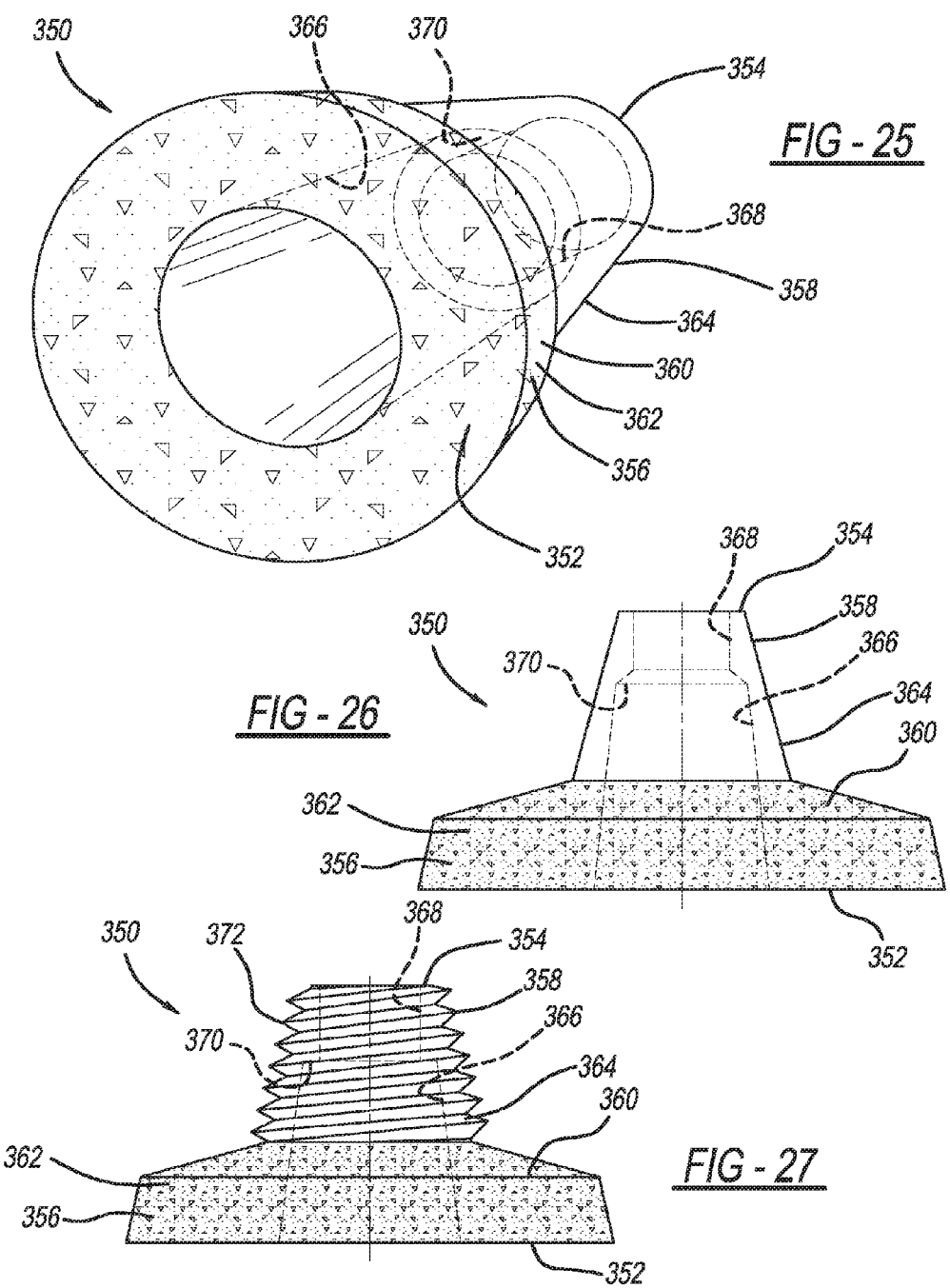

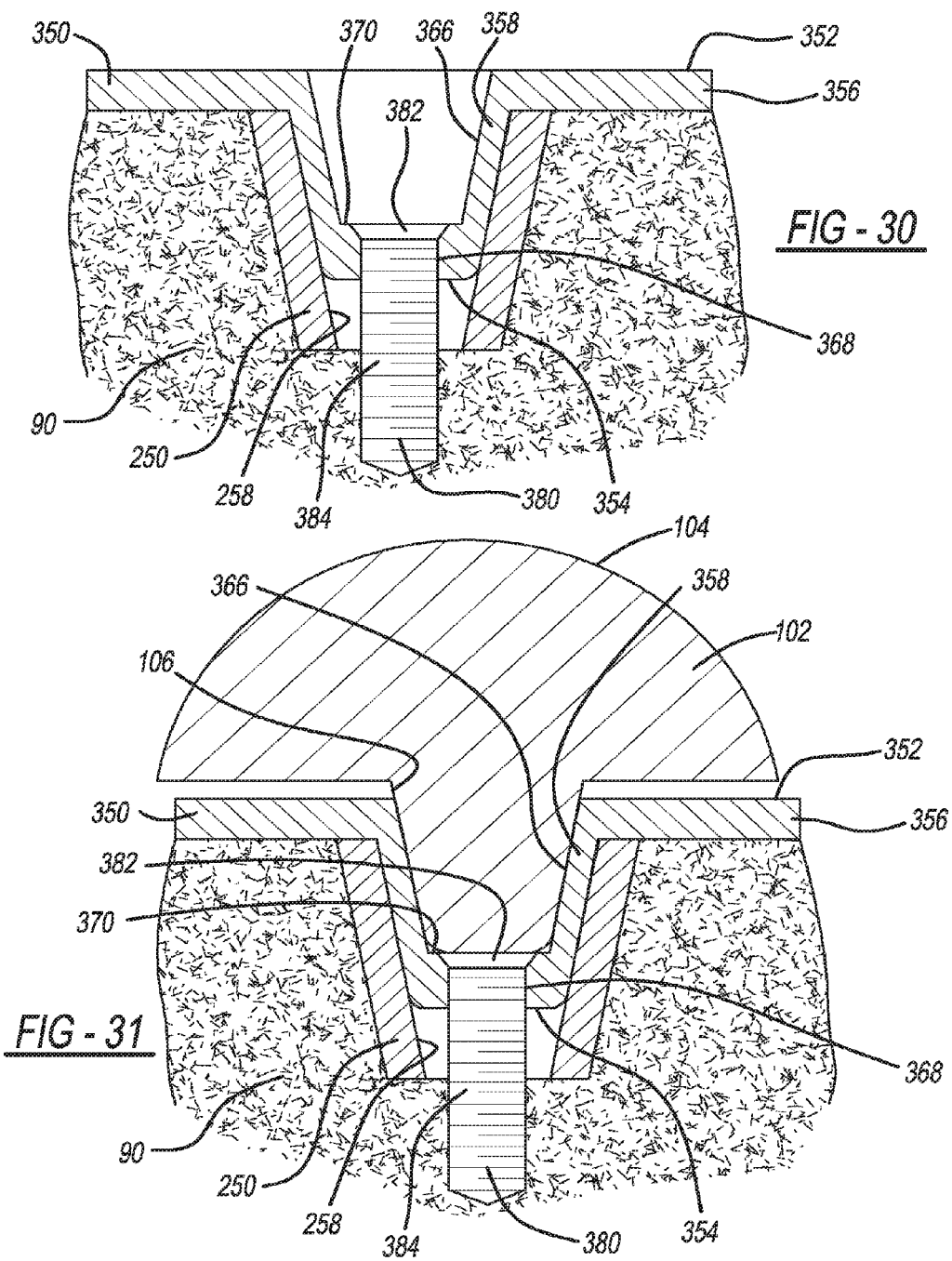

MODULAR GLENOID BASE PLATE WITH AUGMENTS

CROSS-REFERENCE TO RELATED APPLICATION

This application is a continuation of U.S. patent application Ser. No. 14/028,930, filed Sep. 17, 2013, now U.S. Pat. No. 9,668,873, issued on Jun. 6, 2017, which application claims the benefit of U.S. Provisional Application No. 61/775,119 filed on Mar. 8, 2013, the entire disclosure of which is incorporated herein by reference.

FIELD

The present disclosure relates to a modular glenoid base plate with augments.

BACKGROUND

This section provides background information related to the present disclosure, which is not necessarily prior art.

Bone at an implant site may be damaged for various reasons, such as due to trauma or bone degeneration caused by age or genetic defect. Implants, such as shoulder implants used in a primary total shoulder replacement or a reverse shoulder replacement, typically require a substantial amount of existing bone at the implant site for the implants to be securely fastened to bone. When the bone loss is great, it may thus be difficult to secure the implants in position. A device and method for securing an implant at an implant site that has experienced significant bone degradation and loss would therefore be desirable

SUMMARY

This section provides a general summary of the disclosure, and is not a comprehensive disclosure of its full scope or all of its features.

The present teachings provide for an implant assembly comprising a bone augment and an articulating member. The bone augment includes a bone-engaging surface and a coupling surface. The articulating member is configured to couple with the bone augment.

The present teachings also provide for an implant assembly including a bone augment, an adapter, and an articulating member. The bone augment includes a bone-engaging surface and an adapter interface. The adapter is configured to connect to the bone augment at the adapter interface. The adapter includes a coupling member. The articulating member is configured to couple with the adapter at the coupling member.

The present teachings further provide for a method for implanting an implant assembly. The method includes filling a bone defect with a bone augment including a bone-engaging surface and a coupling surface, and coupling an articulating member to the coupling surface.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1 is a perspective view of a bone augment according to the present teachings;

FIG. 2 is a lateral view of the bone augment of FIG. 1;

FIG. 3 is a perspective view of an adapter according to the present teachings, the adapter configured to couple with the bone augment of FIG. 1;

FIG. 4 is a lateral view of the adapter;

FIG. 5 is a perspective view of the bone augment and the adapter showing how the adapter is coupled to the bone augment;

FIG. 6 is a lateral view of the adapter fastened to the bone augment;

FIG. 11 is a perspective view of an additional bone augment according to the present teachings;

FIG. 12 is a perspective view of another adapter according to the present teachings;

FIG. 15 is a cross-sectional view taken along line 15-15 of FIG. 14;

FIG. 16 is a perspective view of another bone augment according to the present teachings;

FIG. 17 is a side view of the bone augment of FIG. 16;

FIG. 18 is a cross-sectional view taken along line 18-18 of FIG. 17;

FIG. 21 is a perspective view of a further bone augment according to the present teachings;

FIG. 22 is a top view of the bone augment of FIG. 21;

FIG. 25 is a perspective view of a base plate according to the present teachings;

FIG. 26 is a side view of the base plate of FIG. 25;

FIG. 27 is a side view of an additional base plate according to the present teachings;

FIG. 30 is a cross sectional view of the bone augment of FIG. 16 implanted in the glenoid, and the base plate of FIG. 26 coupled to the bone augment;

FIG. 31 is a cross-sectional view similar to FIG. 30, but further includes an articulating member coupled to the base plate;

Corresponding reference numerals indicate corresponding parts throughout the several views of the drawings.

DETAILED DESCRIPTION

Figure 7:
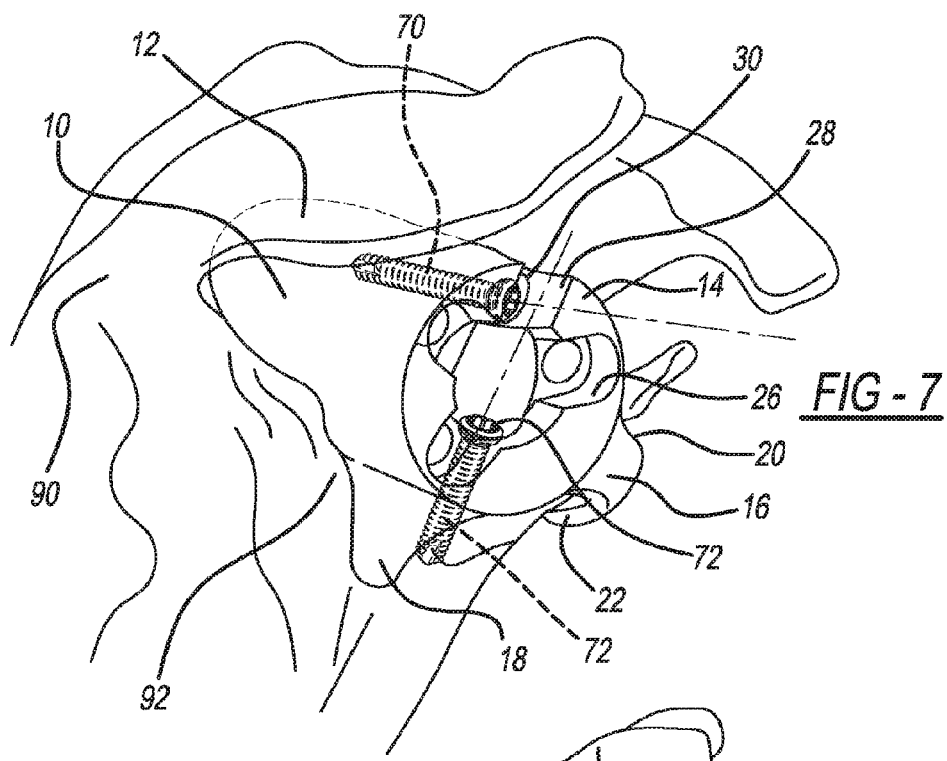
FIG. 7 is a perspective view of the bone augment implanted in a scapula bone.

Example embodiments will now be described more fully with reference to the accompanying drawings.

With initial reference to FIGS. 1 and 2, a bone augment according to the present teachings is generally illustrated at reference numeral 10. The bone augment 10 includes a bone-engaging surface 12 and an adapter interface 14. The bone-engaging surface 12 can have any suitable size and shape to fill a bone defect at an implant location for the bone augment 10, such as either a patient's glenoid or humerus. For example, the bone-engaging surface 12 can be a patient-specific surface sized and shaped to fill and be complimentary to a bone defect of a specific patient.

The patient's bone defect can thus be modeled or mapped using suitable modeling or mapping techniques, such as those described in U.S. patent application Ser. No. 13/653,886 filed on Oct. 17, 2012, and assigned to Biomet Manufacturing Corporation of Warsaw, Ind., which is incorporated by reference herein. For example, computer modeling for obtaining three-dimensional (3D) images of the patient's anatomy using magnetic resonance imaging (MRI) or computed tomography (CT) of the patient's anatomy, and the patient-specific prosthesis components can be designed using various CAD programs and/or software. The patient-specific implants, such as the bone augment 10, can be generally designed and formed using computer modeling based on 3D anatomic image(s) generated from an x-ray, MRI, CT, ultrasound or other medical scans.

Specifically, an anatomical feature (e.g., a glenoid with or without surrounding soft tissue) can be imaged to detect certain features of the anatomy (e.g., dimensions, curvature of surfaces, etc.). The patient-specific implant, and/or augment 10, can have a three-dimensional engagement surface that is complementary and made to conformingly contact the anatomical surface. Thus, the patient-specific implants can be configured to fit at only one position to the anatomical surface. The geometry, shape and orientation of the various features of the patient-specific implants, can be determined during the pre-operative planning stage of the procedure in connection with the computer-assisted modeling of the patient's anatomy. During the pre-operative planning stage, patient-specific implants can be manufactured and selected with input from a surgeon or other professional associated with the surgical procedure.

As used herein, the terms "patient-specific," "custom-made," or "customized" are defined to apply to implants that include certain geometric features, including surfaces, curves, or other lines, and which are made to closely conform as mirror-images or negatives or complementary surfaces of corresponding geometric features or anatomic landmarks of a patient's anatomy obtained or gathered during a pre-operative planning stage based on 3D computer images of the corresponding anatomy reconstructed from image scans of the patient by computer imaging methods. Further, patient-specific features, such as screw holes, guiding apertures, guiding slots, or other holes or openings that are included in implants are defined as features that are made to have positions, orientations, dimensions, shapes and/or define axes specific to the particular patient's anatomy including various anatomic or mechanical axes based on the computer-assisted pre-operative plan associated with the patient, or for directing bone screws into appropriate healthy bone. The various patient-specific implants can be made of any biocompatible material, including, polymer, ceramic, metal or combinations thereof.

More specifically, the present teachings provide various embodiments of shoulder implants and patient-specific bone augments. The shoulder implants and patient-specific bone augments of the present teachings can have patient-specific engagement surfaces that reference various portions of the shoulder joint.

Patient-specific augments according to the principles of the present disclosure are used to repair a defect in an anatomical feature such as a void in a glenoid fossa due to severe wear or dysplasia. Each augment is designed for the unique anatomy of a specific patient based on a 3D model. The 3D model is generated based on imaging data obtained using a medical imaging technique such as a CT scan or a MRI.

In one example, a 3D model of a mold for an implant is created based on the imaging data, and the mold is formed based on the 3D model. A surgeon may then use the mold to form an implant or augment. The mold may be a two-piece mold that allows a surgeon to insert bone graft or any suitable biocompatible material into the mold and then apply pressure to the mold to form the implant. In another example, a 3D model of the implant is created based on the imaging data. The implant and/or a replica of the implant may then be directly formed based on the 3D model thereof. The surgeon may create the implant based on the 3D model and/or the replica of the implant.

Creating the implant based on a 3D model of a specific patient's anatomy ensures that the implant accurately conforms to a defect and fills the defect to provide a continuous surface with the surface surrounding the defect. Thus, the natural movement of a shoulder joint, including glenoid version, may be reproduced. In addition, a surgeon may create the implant pre-operatively, which reduces the amount of time that the surgeon may spend in an operating room. The guides and implants described herein may be used for both anatomic and reverse shoulder joint replacements. The bone-engaging surface 12 can include both a first flange 16 and a second flange 18 extending from the bone-engaging surface 12. The first flange 16 can include a first portion 20 and a second portion 22. The first portion 20 extends generally in a first direction, and the second portion 22 extends generally in a second direction that is angled at about 90 degrees to the first direction. The first flange 16 and the second flange 18 can be provided with any shape and size suitable to match a patient's bone defect, thereby further customizing the bone augment 10 to fill the patient's bone defect and maintain the bone augment 10 at a predetermined location. For example, the first flange 16 and the second flange 18 can prevent the bone augment 10 from rotating at an implant site. The first and second flanges 16 and 18 can extend to any bone surrounding the glenoid including—but not limited to—the coracoid process, acromion, lateral scapular spine, inferior scapular spine, posterior plane of the scapula and anterior portion of the scapula. The first and second flanges 16 and 18 provide: additional locations for bone screws providing increased initial fixation of the component, and increased stability of the implant as the flanges will evenly distribute the kinematic loads of the shoulder as well as provide an increased surface area for biological fixation. Any suitable number of flanges can be provided in addition to the first and the second flanges 16 and 18.

The bone augment 10 defines a center bore 24 that extends from the adapter interface 14 into the bone augment 10. Arranged about the center bore 24 at the adapter interface 14 is an adapter recess 26, which is generally a recessed surface at the adapter interface 14. At the adapter interface 14 is also a recess or notch 28 in the bone augment 10. At the notch 28 is a first bone screw bore 30, which extends from the notch 28 and through the bone-engaging surface 12, and is configured to receive a fastener to secure the bone augment 10 at an implant site, as described herein.

A second bone screw bore 32 is located at the center bore 24 and extends from the center bore 24 through the augment 10. The second bone screw bore 32 is configured to receive an additional fastener for securing the bone augment 10 at an implantation site. The first and second bone screw bores 30 and 32 can be non-threaded or threaded, as illustrated in FIG. 2, for example. The first and second bone screw bores 30 and 32 can be provided at any suitable angle or position within the bone augment 10 to enhance fixation of the bone augment at an implantation site with fasteners seated in the first and second bone screw bores 30 and 32.

At the adapter interface 14, the bone augment 10 further includes a first adapter retention bore 34, a second adapter retention bore 36, and a third adapter retention bore 38. Each of the first, second, and third adapter retention bores 34, 36, and 38 are seated in the adapter recess 26 and are positioned about the center bore 24. The first, second and third adapter retention bores 34, 36 and 38 can be positioned and spaced apart about the center bore 24 in any suitable manner in order to accommodate, for example, the adapter 50 of FIG. 3.

For example and as illustrated in FIGS. 1 and 2, the second and third adapter retention bores 36 and 38 are positioned closest to one another, and the first adapter retention bore 34 is arranged such that the second and third adapter retention bores 36 and 38 are closer together as compared to the distance between the first adapter retention bore 34 and the second adapter retention bore 36, as well as compared to the distance between the first adapter retention bore 34 and the third adapter retention bore 38. Each of the first, second, and third adapter retention bores 34, 36, and 38 can be threaded to accommodate a suitable fastener, such as a screw. The bone augment 10 can be made of any suitable biocompatible material, such as any suitable polymeric or metallic material. A porous metallic material can be used, such as Regenerex® by Biomet of Warsaw, Ind.

With additional reference to FIGS. 3 and 4, the adapter 50 will now be described in detail. The adapter 50 includes a main body 52, which defines a tapered receptacle 54. The tapered receptacle 54 provides a coupling member for coupling various implants to the bone augment 10 by way of the adapter 50, as described herein. Extending from the main body 52 is a first fastener flange 56, a second fastener flange 58, and a third fastener flange 60. The first fastener flange 56 defines a first aperture 62, the second fastener flange 58 defines a second aperture 64, and the third fastener flange 60 defines a third aperture 66. The first, second, and third fastener flanges 56, 58 and 60 are spaced apart about the main body 52 to any suitable position in order to correspond to the location of the first, second, and third adapter retention bores 34, 36, and 38 of the adapter interface 14, for example. The first, second, and third apertures 62, 64, and 66 are each sized and arranged to receive a suitable fastener therethrough such that the fasteners can be received by one of the first, second, or third adapter retention bores 34, 36, and 38 in order to secure the adapter 50 to the bone augment 10.

With additional reference to FIGS. 5 and 6, a first bone fastener 70 and a second bone fastener 72 configured to secure the bone augment 10 to bone at an implantation site are illustrated. Any suitable fastening device can be used, such as an elongated bone screw. The first bone fastener 70 is configured to be received by, and extend through, the first bone screw bore 30. The second bone fastener 72 is configured to be received by, and extend through, the second bone screw bore 32.

The first and second bone screw bores 30 and 32 can be positioned and angled in any suitable manner to direct the first and second bone fasteners 70 and 72 to a desired location at the implant site. For example, the first and second bone screw bores 30 and 32 can be oriented to maximize retention of the fasteners 70 and 72 to bone at the implant site, in order to maximize retention of the bone augment 10 at the implant site. For example, the first and second bone screw bores 30 and 32 can have a patient-specific orientation and position to direct the first and second fasteners 70 and 72 to an optimal position based on the patient's anatomy in order to secure the bone augment 10 at the patient's defect site. The adapter 50 can be made of any suitable material, such as any suitable biocompatible metal.

The adapter 50 is secured at the adapter interface 14 with a first insert fastener 74 extending through the first aperture 62 of the adapter 50 and into the first adapter retention bore 34. Similarly, a second insert fastener 76 is inserted through the second aperture 64 and into the second adapter retention bore 36, and a third insert fastener 78 is inserted through the third aperture 66 and into the third adapter retention bore 38.

The adapter 50 can be provided in a variety of stock sizes, in contrast to the bone augment 10, which can be provided with a patient-specific size and shape to closely match the patient's anatomy. For example, the bone augment 10 can be provided in overall small, medium, and large sizes, which can be selected based on the patient-specific size of the bone augment 10. Therefore, the adapter 50 allows any suitably sized stock implant, such as a glenosphere, to be coupled to the patient-specific bone augment 10 regardless of its size and shape, as described herein.

Figure 8:
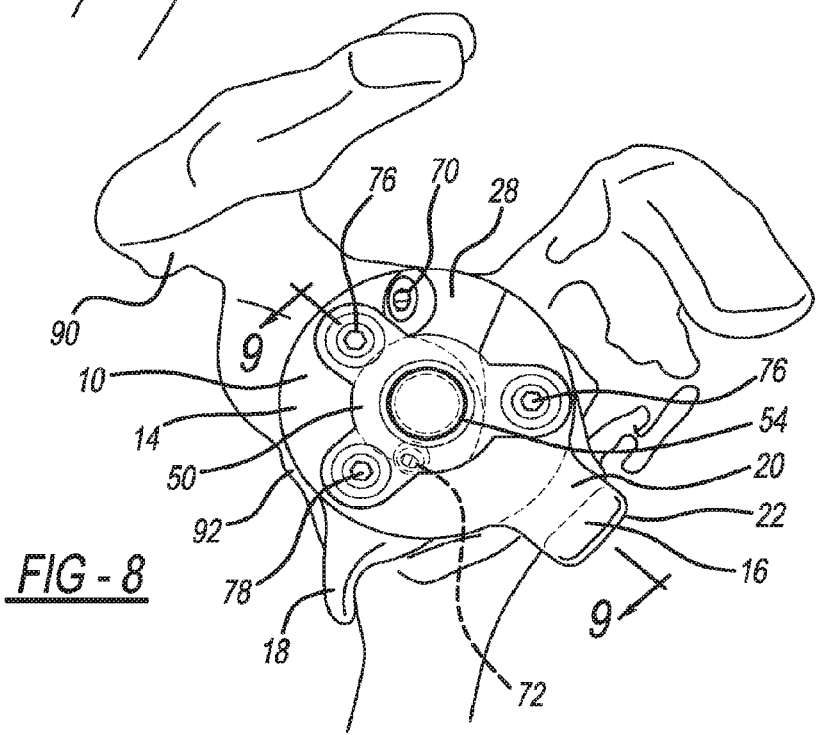
FIG. 8 is a lateral view of the bone augment with the adapter fastened thereto implanted in the scapula bone.

The bone augment 10 can be implanted at any suitable bone defect site. For example and with reference to FIGS. 7 and 8, the bone augment 10 can be implanted in a scapula bone 90 to fill a defect at glenoid 92. The bone-engaging surface 12 extends into the glenoid 92, and the first and second flanges 16 and 18 overlap a portion of the scapula bone 90 proximate to the glenoid 92, so as to restrict rotation of the bone augment 10. The first and second bone fasteners 70 and 72 extend through the first and second bone screw bores 30 and 32 respectively, and into the scapula bone 90 to secure the bone augment 10 to the scapula bone 90. As illustrated in FIG. 8, the adapter 50 is coupled to the bone augment 10 at the adapter interface 14 to provide a coupling member for an implant in order to couple the implant to the bone augment 10 by way of the adapter 50, the coupling member provided by the tapered receptacle 54 of the adapter 50. Together, the bone augment 10 and the adapter 50 provide an implant assembly suitable for coupling an implant to an implant site with a bone defect including a patient-specific (i.e., custom) bone augment 10, and a standardized adapter 50.

Figure 9:
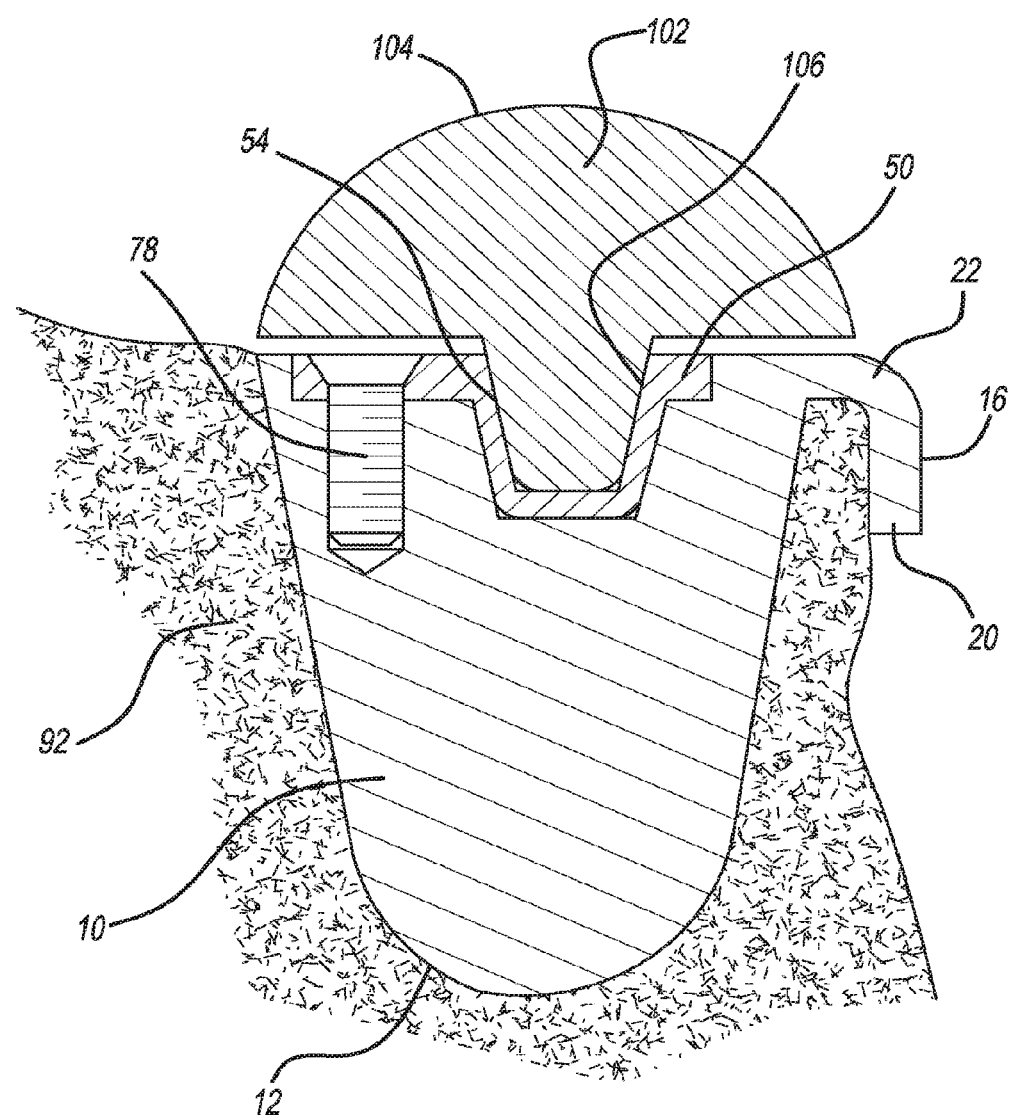
FIG. 9 is a cross-sectional view of FIG. 8 of an articulating member coupled to the adapter.

With reference to FIG. 9, an articulating member 102 can be coupled to the adapter 50 and thus included as part of the implant assembly. More specifically, the articulating member 102 includes a convex articulating surface 104 and a stem 106. The stem 106 is tapered and corresponds to the tapered receptacle 54 of the adapter 50 such that when the stem 106 is inserted within the tapered receptacle 54, the stem 106 can be coupled to the adapter 50 such as by way of a Morse taper connection between the stem 106 and the tapered receptacle 54. The articulating member 102 can be any suitable articulating member such as a glenosphere of a shoulder implant, such that connection of the articulating member 102 to the bone augment 10 by way of the adapter 50 provides a reverse shoulder implant assembly when the bone augment 10 is implanted at glenoid 92. The stem 106 may be integral and monolithic with the articulating member 102, or may be the stem of an intermediate member between the articulating member 102 and the adaptor 50, such as a Versa-Dial™ adaptor by Biomet of Warsaw, Ind. The bone augment 10 with the articulating member 102 coupled thereto can also be coupled in a humerus. The articulating member 102 can be made of any suitable biocompatible material, such as a suitable metallic or polymeric material.

Figure 10:
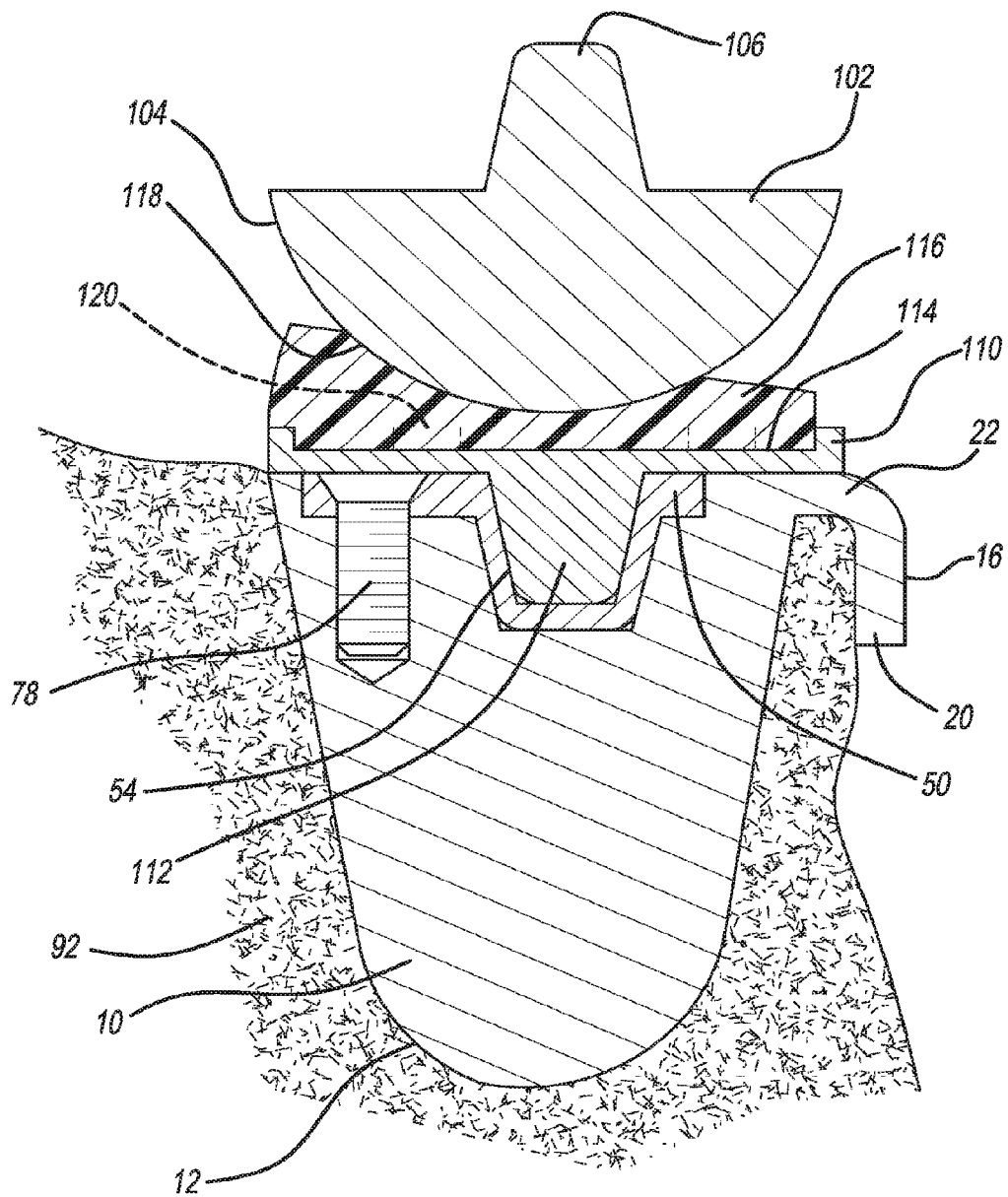
FIG. 10 is a cross-sectional view with a base plate and a bearing coupled to the adapter, the bearing in articulating cooperation with an articulating member.

With additional reference to FIG. 10, for a primary shoulder implant assembly a base plate 110 can be coupled to the adapter 50. The base plate 110 includes a base plate stem 112 and a planar surface 114 opposite thereto. The base plate stem 112 is seated within the tapered receptacle 54 of the adapter 50 to connect the base plate 110 to the adapter 50 with, for example, a Morse taper. Coupled to the planar surface 114 is a bearing 116, which includes a concave articulating surface 118. The bearing 116 can be made of any suitable material, such as a polymeric material. The bearing 116 can be coupled to the planar surface 114 in any suitable manner, such as through interaction between flanges 120 extending from the planar surface 114 of the base plate 110 and the bearing 116. The flanges 120 can couple the bearing 116 to the planar surface 114 in any suitable manner, such as by interaction between the flanges 120 and a recess or indentation of the bearing 116. The bearing 116 can articulate with a suitable articulating member, such as the articulating member 102 coupled to a patient's humerus, thereby providing a primary shoulder implant in which the bearing 116 provides a glenoid articulating surface at the glenoid 92, and thus a primary shoulder implant. The bone augment 10 with the base plate 110 and the bearing 116 coupled thereto can also be implanted in a patient's humerus for a reverse total shoulder implant.

With reference to FIG. 11, another bone augment according to the present teachings is illustrated at reference numeral 150. The bone augment 150 generally includes a bone-engaging surface 152 and an adapter interface 154. The bone-engaging surface 152 is generally opposite to the adapter interface 154. The bone-engaging surface 152 includes a first flange 156 and a second flange 158 extending therefrom. Like the bone-engaging surface 12 of the bone augment 10, the bone-engaging surface 152 of the bone augment 150 can be a patient-specific surface, sized and shaped to be seated in and fill a bone defect of a specific patient. The first flange 156 and the second flange 158 can be oriented and shaped to engage a patient's bone defect at any suitable location to replace bone at the defect and restrict rotation of the bone augment 150.

At an approximate center of the bone augment 150 is a center or first bone screw bore 160 defined by the bone augment 150. The bone augment 150 further includes a second bone screw bore 162, a third bone screw bore 164, and a fourth bone screw bore 166. The first, second, third, and fourth bone screw bores 160-166 can be located at any suitable location of the bone augment 150 and can be oriented at any suitable angle to direct fasteners, such as bone screws, extending therethrough into bone at a bone defect to secure the bone augment 150 at the bone defect in order to replace missing bone, as explained in detail herein. The first, second, third, and fourth bone screw bores 160-166 can thus have a custom orientation to direct the fasteners into the patient's healthy bone.

The bone augment 150 further includes an adapter recess 170, which surrounds the first bone screw bore 160. The adapter recess 170 is generally a recessed portion of the adapter interface 154, and is configured to receive an adapter 180, illustrated in FIG. 12, as further described herein. The first bone screw bore 160 extends from the adapter recess 170 to the bone-engaging surface 152. The second bone screw bore 162 also extends from the adapter recess 170 through the bone augment 150 to the bone-engaging surface 152. The third and fourth bone screw bores 164 and 166 are spaced apart from the adapter recess 170, and extend from the adapter interface 154 through the bone augment 150 to the bone-engaging surface 152. Alternatively, the first, second, third, and fourth bone screw bores 160-166 can be arranged at any suitable location on the bone augment 150 and be oriented at any suitable angle to direct bone screws to desired locations in bone as described herein.

The bone augment 150 further includes first, second, and third adapter retention bores 172, 174, and 176. The first, second and third adapter retention bores 172, 174 and 176 can be spaced apart at any location at the bone-engaging surface 152 and configured to receive any suitable fastener in order to retain the adapter 180 to the adapter interface 154 of the bone augment 150, as further described herein.

With reference to FIG. 12, the adapter 180 generally includes a main body 182, a first surface 184, and a second surface 186, which is opposite to the first surface 184. The first and second surfaces 184 and 186 are generally planar. The adapter 180 defines a tapered receptacle 188. An opening of the tapered receptacle 188 is defined at the first surface 184. The tapered receptacle 188 extends through the main body 182 and extends from the second surface 186. The tapered receptacle 188 is tapered such that its diameter is greatest at the first surface 184, and the diameter gradually becomes smaller as the tapered receptacle 188 extends from the second surface 186. The diameter of the tapered receptacle 188 is smallest at a portion of the tapered receptacle 188 that is most distal to the second surface 186. The adapter 180 further includes a first aperture 190, a second aperture 192, and a third aperture 194. Each of the first, second and third apertures 190, 192, and 194 are defined by the main body 182, and each extend between the first surface 184 and the second surface 186 of the main body 182 in order to receive a suitable fastener therethrough for coupling the adapter 180 to the bone augment 150. The first, second and third apertures 190, 192, and 194 are thus arranged to align with the first, the second, and the third adapter retention bores 172, 174 and 176. Like the adapter 50, the adapter 180 can be provided in a variety of standard stock sizes and shapes to cooperate with the bone augment 150, such as small, medium, and large. Therefore, the adapter 180 can couple any suitable standardized or patient-specific implant, such as the articulating member 102 or the base plate 110, to the patient-specific bone augment 150.

Figures 13, 14:
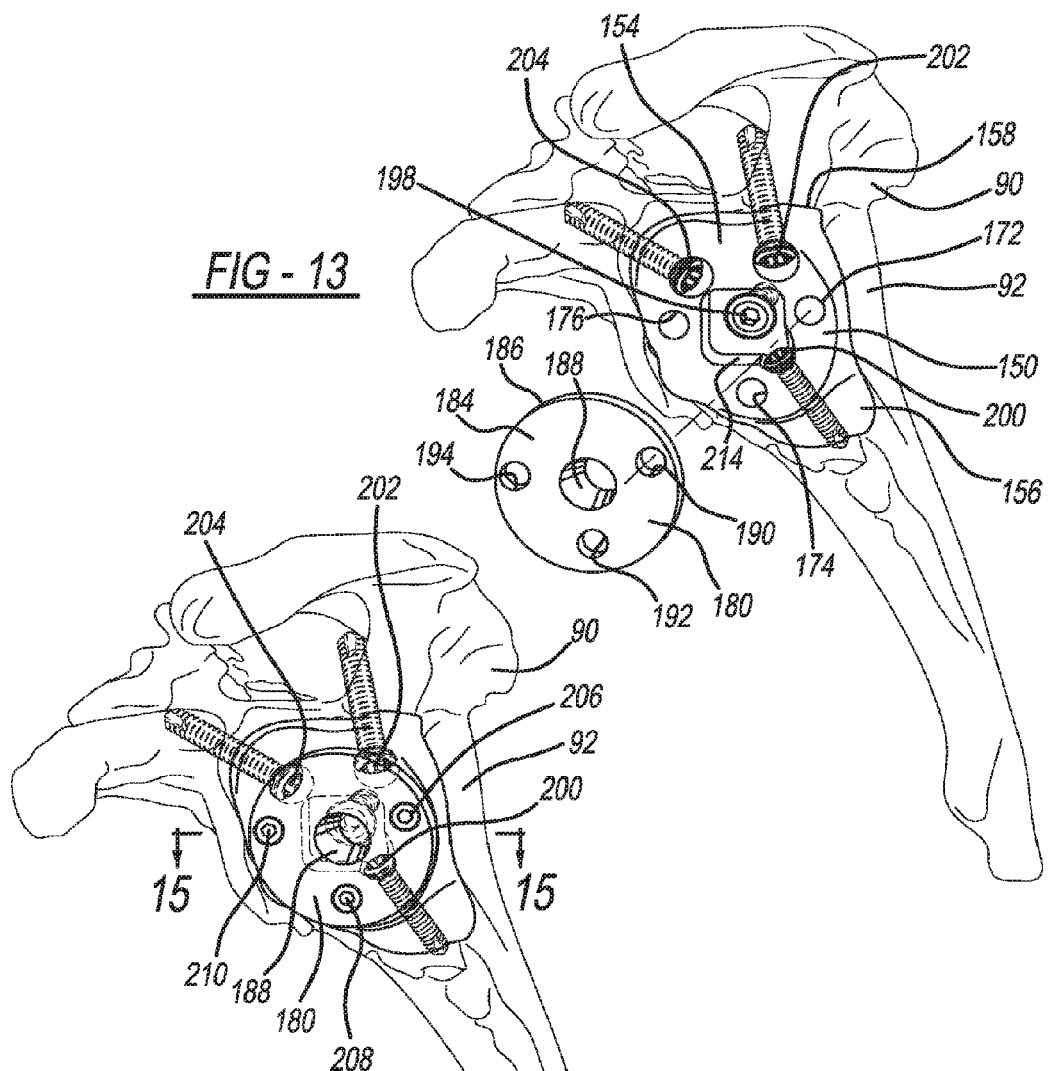
FIG. 13 is a perspective view of the bone augment of FIG. 11 implanted in a scapula bone at a glenoid thereof.
FIG. 14 illustrates the bone augment of FIG. 11 implanted in the scapula bone, and the adapter of FIG. 12 coupled to the bone augment.

With additional reference to FIGS. 13 and 14, the bone augment 150 can be implanted in any suitable bone to fill a defect therein, such as in the scapula 90 in order to fill a defect at the glenoid 92. Specifically, a first bone screw 198 is inserted through the first bone screw bore 160 of the bone augment 150 and into the glenoid 92 to secure the bone augment 150 to the glenoid 92. Similarly, a second bone screw 200 is inserted through the second bone screw bore 162, a third bone screw 202 is inserted through the third bone screw bore 164, and a fourth bone screw 204 is inserted through the fourth bone screw bore 166. The first, second, third, and fourth bone screw bores 160-166 are positioned and angled to direct each of the first, second, third, and fourth bone screws 198-204 to desired positions in the scapula 90 according to the patient's particular bone defect in order to maximize retention of the bone augment 150 at the glenoid 92.

The adapter 180 is seated against the adapter interface 154 and secured thereto with a first adapter screw 206 extending through the first aperture 190 and into the first adapter retention bore 172, a second adapter screw 208 extending through the second aperture 192 and into the second adapter retention bore 174, and a third adapter screw 210 extending through the third aperture 194 and into the third adapter retention bore 176, as illustrated in FIG. 14.

With reference to FIG. 15, the adapter 180 includes a generally square flange 212 extending from the second surface 186, which generally surrounds and is opposite to the tapered receptacle 188. The square flange 212 is sized and shaped to be complementary with the adapter recess 170, which includes a generally square sidewall 214 (see FIG. 11, for example). The adapter 180 is seated against the adapter interface 154 such that the square flange 212 sits within the adapter recess 170 and abuts the square sidewall 214 thereof. This interaction between the square flange 212 and the adapter recess 170 helps restrict rotation of the adapter 180 with respect to the bone augment 150. Although the adapter recess 170 and the flange 212 are illustrated as square, they can be of any other suitable shape.

Any suitable implant can be coupled to the bone augment 150 by way of the adapter 180. For example, the articulating member 102 can be connected to the adapter 180, such as with a taper lock, by inserting the stem 106 of the articulating member 102 into cooperation with the tapered receptacle 188. Coupling the articulating member 102 to the adapter 180 will provide an implant assembly for a reverse shoulder arthroplasty. Furthermore, the base plate 110 with the bearing 116 coupled thereto (as illustrated in FIG. 10) can be coupled to the adapter 180 to provide an implant assembly for a primary shoulder arthroplasty in which the convex articulating surface 118 is provided at the glenoid 92, and the articulating member 102 is mounted to the humerus. The bearing 116 can also articulate with a natural humeral head of the humerus.

With additional reference to FIGS. 16-18, another bone augment according to the present teachings is generally illustrated at reference numeral 250. The bone augment 250 generally includes a first end 252 and a second end 254, which is opposite to the first end 252. The bone augment 250 further includes a bone-engaging surface 256 extending between the first end 252 and the second end 254. Opposite to the bone-engaging surface 256 is a coupling surface 258. The bone augment 250 is generally shaped as a conical sleeve. Therefore, the bone-engaging surface 256 is generally conical and tapers inward from the first end 252 to the second end 254. The bone-engaging surface 256 has its greatest diameter at the first end 252 and its smallest diameter at the second end 254. The bone-engaging surface 256 can be smooth or have a porous surface 260, which facilitates bone growth therein.

The coupling surface 258 also tapers inward from the first end 252 to the second end 254. Therefore, the coupling surface 258 has its greatest diameter at the first end 252, and its smallest diameter and the second end 254. The coupling surface 258 generally defines an inner bore 262 that extends through the bone augment 250 from the first end 252 to the second end 254. The bone augment 250 can be provided with any suitable size or shape, such as a plurality of different stock sizes or shapes. For example, the bone augment 250 can be provided with a standard small, medium, and large size. The coupling surface 258 may be threaded and need not be tapered as illustrated, but rather may extend linearly.

The bone augment 250 can be made of any suitable material, such as a suitable biocompatible metallic or a suitable biocompatible polymeric material. The bone augment 250 can be made using any suitable manufacturing process or technique, such as a suitable molding technique or a suitable additive manufacturing technique, such as 3D printing.

Figure 19:
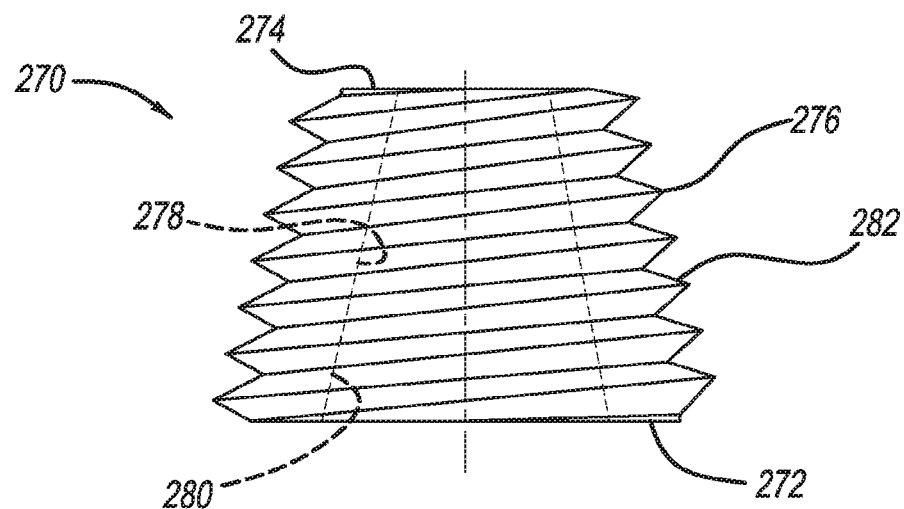
FIG. 19 is a side view of yet another bone augment according to the present teachings.

With additional reference to FIG. 19, another bone augment according to the present teachings is generally illustrated at reference numeral 270. The bone augment 270 includes a first end 272 and a second end 274, which is opposite to the first end 272. A bone-engaging surface 276 is at an outer portion of the bone augment 270 and extends between the first end 272 and the second end 274. Opposite to the bone-engaging surface 276 is a coupling surface 278, which defines an inner bore 280 of the bone augment 270. The coupling surface 278 may be threaded and need not be tapered as illustrated, but rather may extend linearly. Both the bone-engaging surface 276 and the coupling surface are tapered inward from the first end 272 to the second end 274. Therefore, the bone augment 270 is sized such that it has its greatest diameter at the first end 272 and its smallest diameter at the second end 274. The inner bore 280 is thus also tapered from the first end 272 to the second end 274. Extending from the bone-engaging surface 276 are external threads 282, which allow the bone augment 270 to be, for example, screwed into bone in order to implant the bone augment 270.

Figure 20:
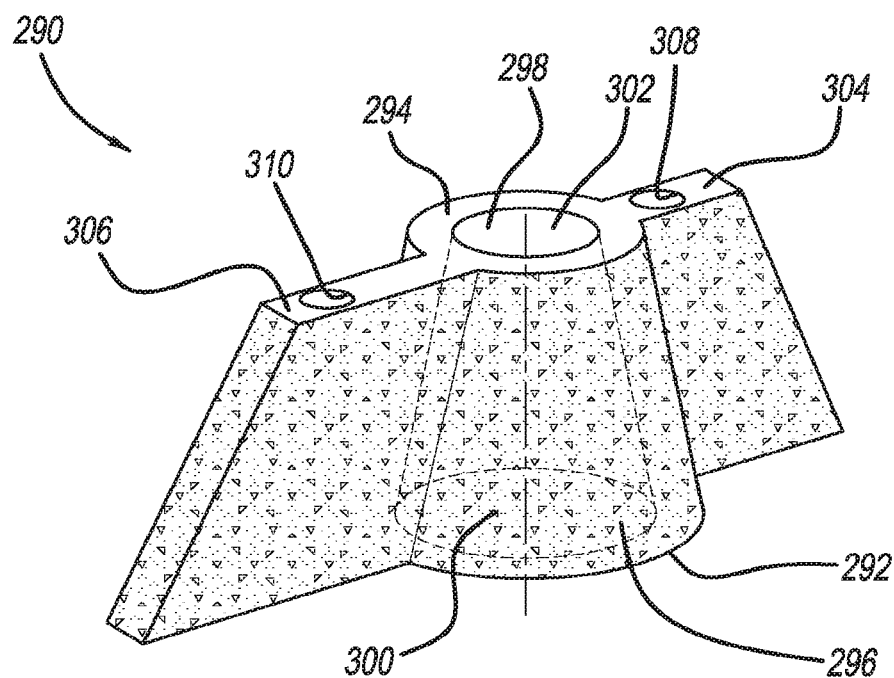
FIG. 20 is a perspective view of an additional bone augment according to the present teachings.

Another bone augment according to the present teachings is illustrated and reference numeral 290 (FIG. 20). The bone augment 290 generally includes a first end 292 and a second end 294. A bone-engaging surface 296 extends from the first end 292 to the second end 294, as does a coupling surface 298. Both the bone-engaging surface 296 and the coupling surface 298 generally taper inward from the first end 292 to the second end 294 to generally provide the bone augment 290 with a conical sleeve. The coupling surface 298 defines an inner bore 302, which extends from the first end 292 to the second end 294. The coupling surface 298 may be threaded and need not be tapered as illustrated, but rather may extend linearly. The bone-engaging surface 296 can be smooth or include a porous surface 300, which facilitates bone growth therein in order to secure the bone augment 290 at a bone defect site.

To further secure the bone augment 290 at a bone defect site, the bone augment 290 includes a first flange 304 and a second flange 306, which extend from opposite sides of the inner bore 302. The first flange 304 and the second flange 306 each include the bone-engaging surface 296 and the porous surface 300. The first flange 304 defines a first bore 308, and the second flange 306 defines a second bore 310. The first bore 308 and the second bore 310 are configured to receive a suitable fastener therethrough in order to enhance retention of the bone augment 290 at an implant site and to prevent rotation or simply secure fixation of the bone augment 290. The bone augment 290 can be oriented at any suitable position at the bone defect site. For example, the first and second flanges 304 and 306 can be positioned such that they are aligned along a line that extends directly superior and inferior across the glenoid, for example. Although first and second flanges 304 and 306 are illustrated, the bone augment 290 can be provided with any suitable number of flanges arranged in any suitable orientation.

Figure 23:
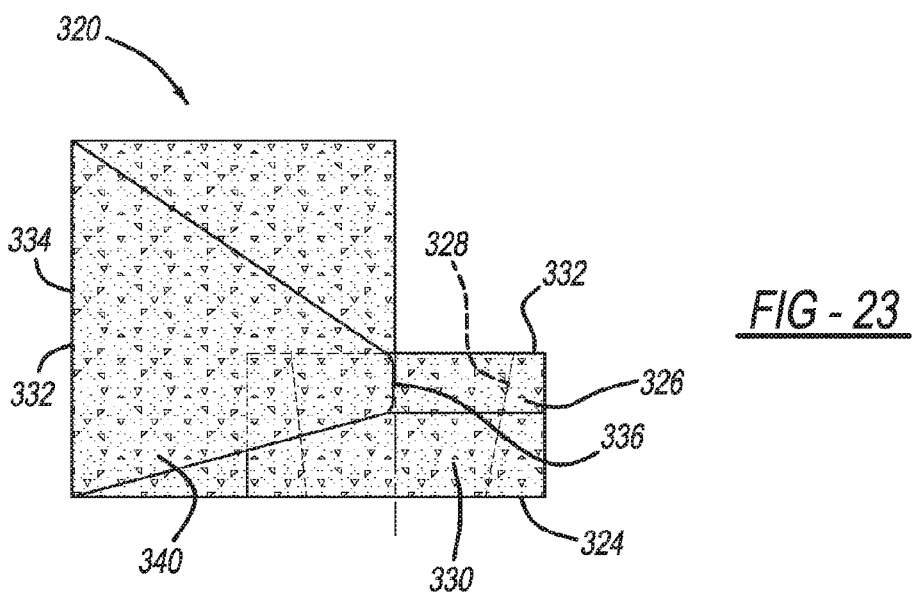
FIG. 23 is a side view of the bone augment of FIG. 21.

With additional reference to FIGS. 21-23, another bone augment according to the present teachings is generally illustrated at reference numeral 320. The bone augment 320 generally includes a first end 322 and a second end 324 opposite thereto. A bone-engaging surface 326 extends between the first end 322 and the second end 324 and is opposite the coupling surface 328. The coupling surface 328 generally tapers inward from the first end 322 to the second end 324. The bone-engaging surface 326 is covered with a porous surface 330 to facilitate bone growth therein. The coupling surface 328 may be threaded and need not be tapered as illustrated, but rather may extend linearly.

A flange 332 extends from the bone-engaging surface 326, and extends approximately 180 degrees about the bone-engaging surface 326. The flange 332 includes an outer surface 334 and an inner surface 336, which abuts and is secured to the bone-engaging surface 326. The inner surface 336 can also be integral with the bone-engaging surface 326. The flange 332 includes a first end 338 and a second end 340 opposite thereto. The outer surface 334 of the flange 332 includes its own bone-engaging surface 342, which may be smooth or include porous surface 330.

Figure 24:
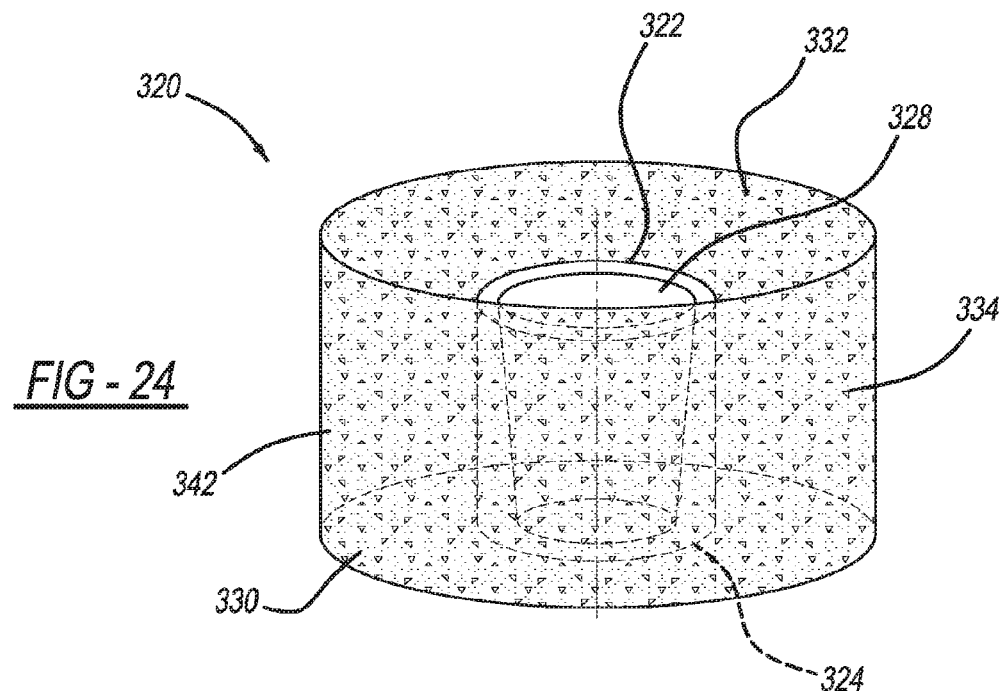
FIG. 24 is a perspective view of still another bone augment according to the present teachings.

The bone augment 320 can be made of any suitable biocompatible material, such as a metallic or polymeric material. The flange 332 can be formed integral with the rest of the bone augment 320, such as through a molding process or through additive manufacturing. The flange 332 can also be formed separately of the rest of the bone augment 320 and mounted to the bone-engaging surface 326 between the first end 322 and the second end 324 in any suitable manner. The flange 332 can extend any suitable distance about the bone-engaging surface 326 in order to fill a particular bone defect at an implantation site. The flange 332 can also be a circular flange that completely surrounds the coupling surface 328, as illustrated in FIG. 24, for example.

With additional reference to FIGS. 25-27, an adapter or base plate according to the present teachings is illustrated at reference numeral 350. As explained herein, the base plate 350 can be coupled with any of the bone augments 250, 270, 290, 320 to secure a suitable implant at an implantation site with a bone defect. The base plate 350 can also be secured directly to bone, such as if bone loss is minimal.

The base plate includes a first end 352 and a second end 354, which is opposite to the first end 352. At the first end 352 is a base 356 and at the second end 354 is a stem 358. Between the base 356 and the stem 358 is an intermediate portion 360, which can be tapered from the base 356 to the stem 358. The base 356 can include a porous outer surface 362 to facilitate bone growth therein and enhance retention of the base plate 350 at an implantation site.

The stem 358 includes a tapered outer surface or coupling surface 364, and a tapered inner surface 366. The tapered inner surface 366 extends from the first end 352 to about a midpoint of the stem 358. The tapered inner surface 366 is tapered inward from the first end 352 to the stem 358, where the tapered inner surface 366 is integral with a fastener bore 368. The fastener bore 368 is defined by the stem 358, and extends from the tapered inner surface 366 to the second end 354 of the stem 358.

A step 370 is formed where the tapered inner surface 366 transitions to the fastener bore 368. The step 370 provides a surface upon which, for example, a head of a fastener can be seated in order to retain the fastener within the stem 358, as further explained herein. The step 370 can taper inward towards the fastener bore 368. As illustrated in FIG. 27, the stem 358 can include threads 372 at the tapered outer surface 364. The threads 372 facilitate implantation of the base plate 350 either directly into bone or cooperation between the stem 358 and the coupling surface 258 of the bone augment 250, or any of the coupling surfaces 278, 298 or 328 described herein, any of which can include internal threads.

Figure 28:
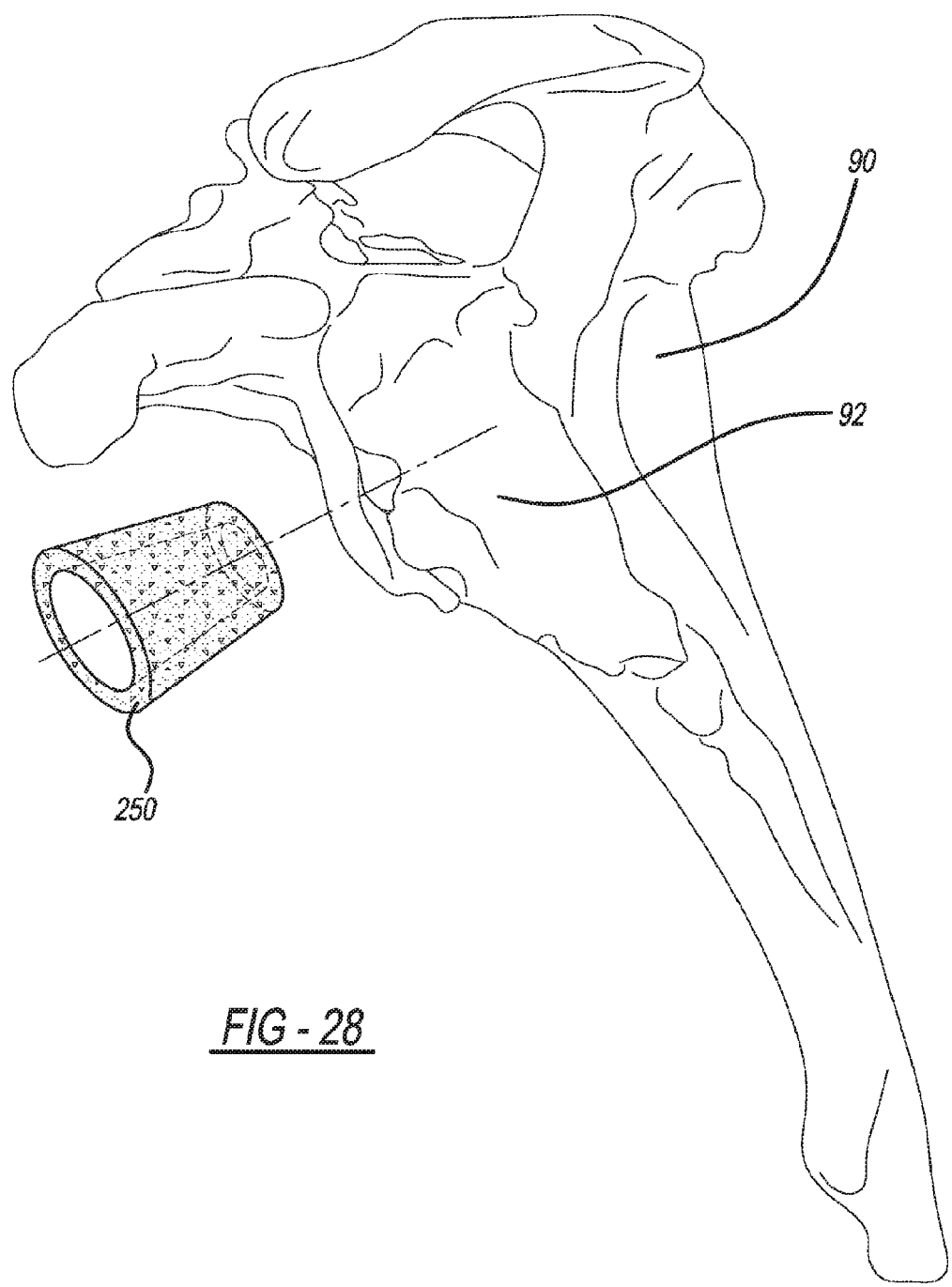
FIG. 28 is a perspective view of a scapula bone and the bone augment of FIG. 16 for implantation at a glenoid of the scapula bone.

With additional reference to FIG. 28, the bone augment 250 can be implanted at any suitable location to fill a bone defect, such as a defect present in scapula bone 90 at glenoid 92. The bone augment 250 can be implanted in any suitable manner and with any suitable tool. For example, the bone augment can be implanted by impaction. Any of the other bone augments described herein can be implanted in any suitable manner as well. For example, the bone augment 270 can be implanted by screwing the external threads 282 of the bone augment 270 into the glenoid 92 by rotating the bone augment 270 using any suitable implantation device. Bone augment 290 with first and second flanges 304 and 306 can be implanted at a bone defect site where added fixation of the bone augment 290 to prevent rotation thereof may be appropriate or desirable. In instances where bone loss at the implantation site is greater, the bone augment 320 can be implanted and positioned such that the flange 332 fills the bone defect. The flange 332 can be any suitable size or shape to fill the bone defect. To fill even larger bone defects, the bone augment 320 of FIG. 24 in which the flange 332 extends entirely about the bone augment 320 can be used.

Figure 29:
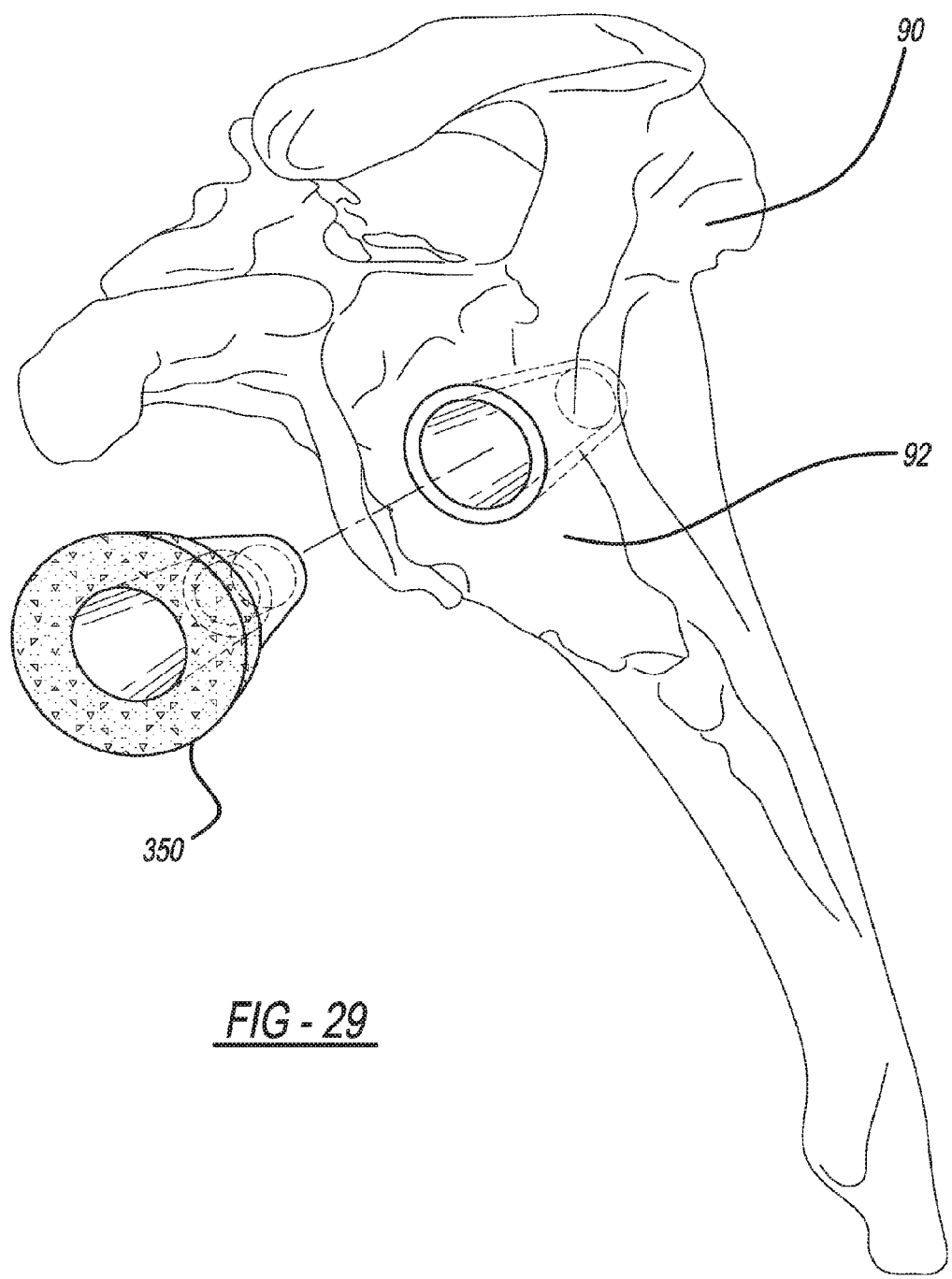
FIG. 29 illustrates the bone augment of FIG. 16 implanted at the glenoid, and illustrates the base plate of FIG. 26 being coupled to the base plate.

After any one of the bone augments 250, 270, 290 or 320 are implanted, the base plate 350 can be coupled thereto, as illustrated in FIG. 29. The base plate 350 is coupled to, for example, the bone augment 250 by inserting the stem 358 of the base plate 350 into the inner bore 262 of the bone augment 250 such that the tapered outer surface 364 abuts the tapered inner surface 366 of the base plate 350 to couple the base plate 350 to the bone augment 250 with a taper lock, as illustrated in FIG. 30. To further secure the base plate 350 to the bone augment 250, and the glenoid 92 for example, a bone screw 380 can be inserted into the fastener bore 368 of the base plate 350 such that a head 382 of the bone screw 380 is seated at step 370 and threads 384 extend into the scapula bone 90.

Figure 32:
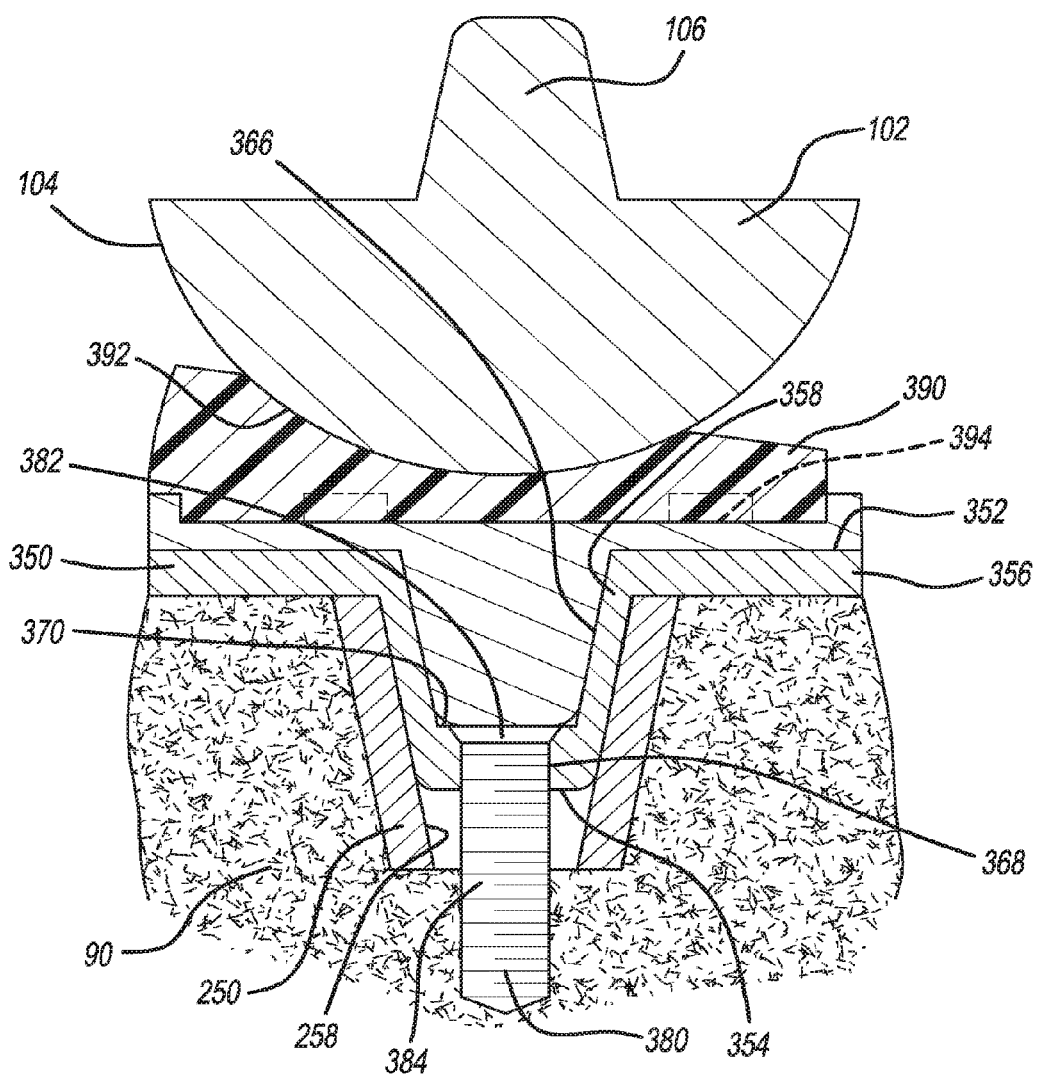
FIG. 32 is a cross-sectional view similar to FIG. 30, but with a bearing coupled to the base plate, the bearing configured to articulate with an articulating member.

With additional reference to FIGS. 31 and 32, the base plate 350 can provide a coupling member for coupling any suitable implant to the base plate 350. For example, and as illustrated in FIG. 31, articulating member 102 can be connected to the base plate 350 through interaction between the stem 106 of the articulating member 102 and the tapered inner surface 366 of the base plate 350. For example, the stem 106 can be coupled to the tapered inner surface 366 with a Morse taper fit.

With reference to FIG. 32, the base plate 350 can include a bearing 390 coupled to the base 356 of the base plate 350 in any suitable manner, such as with a coupling member 394 in the form of a flange extending from the base 356. The bearing 390 can include a concave articulating surface 392 configured to articulate with, for example, articulating member 102, which can be mounted to a humerus bone. In this manner, the bone augment 250 and the bearing 390 provide an implant assembly for a primary shoulder implant.

Figure 33:
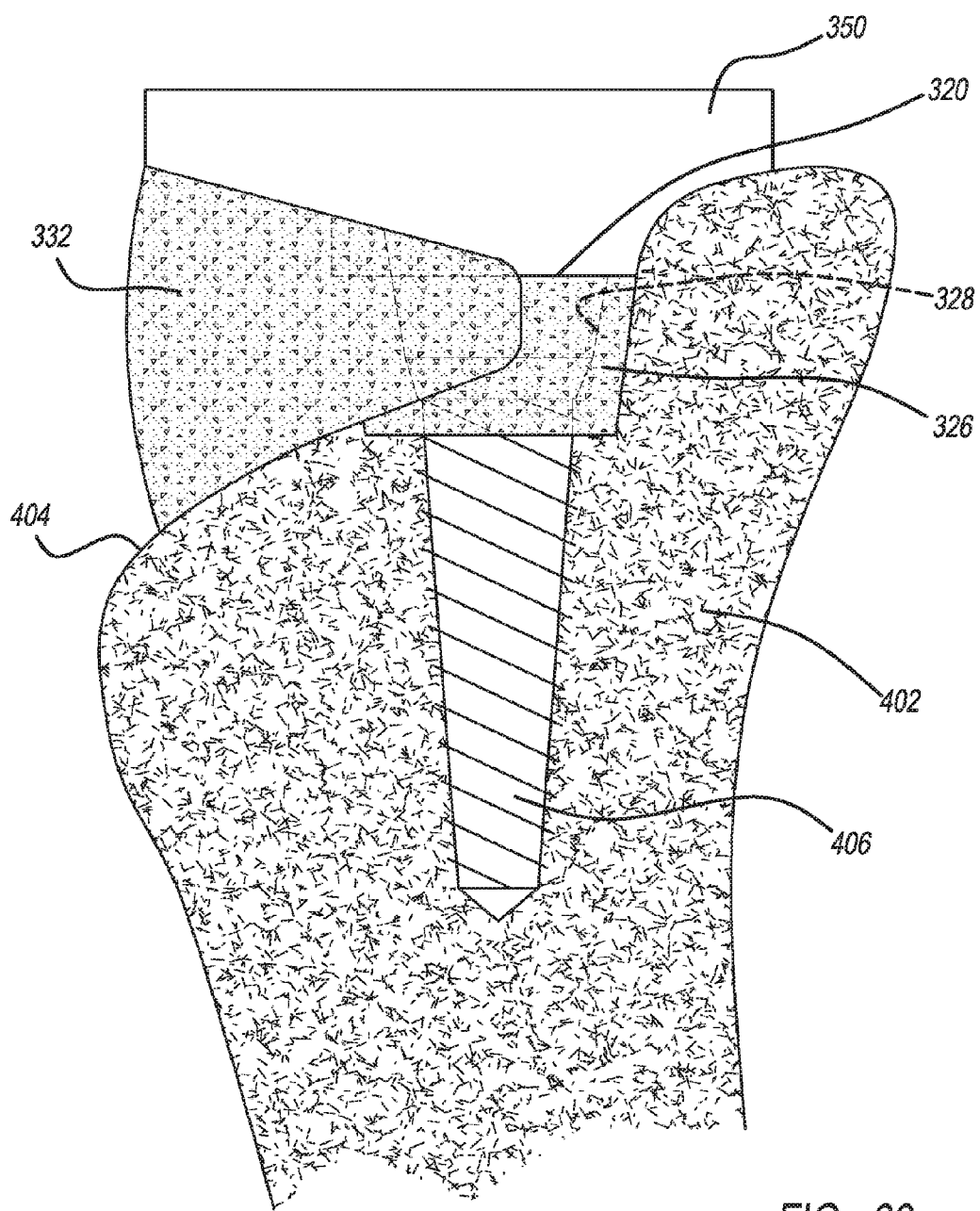
FIG. 33 illustrates the bone augment of FIGS. 21-23 fastened to a bone with an eroded articulating surface, and the base plate of FIG. 26 fastened to the bone augment.

The present teachings can be adapted to fill any bone defect at most any location. For example, and with reference to FIG. 33, a generic bone 402 with an eroded articulating surface 404 can include the bone augment 320 coupled thereto such that the flange 332 takes the place of bone missing from the eroded articulating surface 404. The bone augment 320 can provide a mount for the base plate 350. Specifically, the stem 358 of the base plate 350 can be inserted within the bone augment 320 such that the tapered outer surface 364 mates with the coupling surface 328 to form a Morse taper coupling therebetween. For added fixation, a bone screw 406 can be inserted within the base plate 350 such that the bone screw 406 extends through the fastener bore 368 of the stem 358 and into the bone 402 through the inner surface 336 of the bone augment 320. As the bone screw 406 is tightened, the base plate 350 and the bone augment 320 are compressed against the bone 402. Use of the bone screw 406 will enhance fixation of the bone augment 320 and the base plate 350 to the bone 402, and facilitate healing at the defect site.

Figure 34:
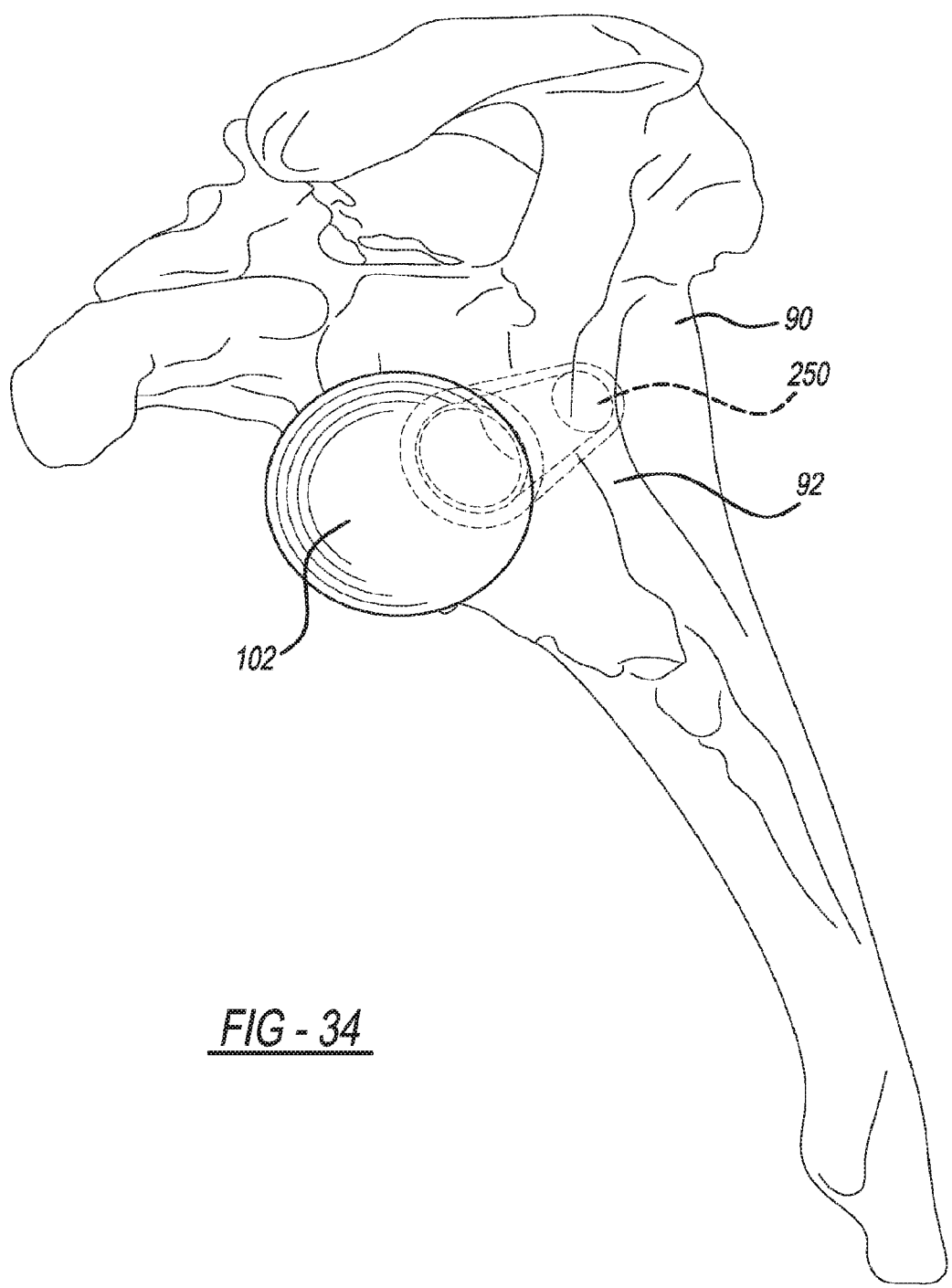
FIG. 34 illustrates the bone augment of FIG. 16 implanted at a glenoid of a scapula bone, and articulating member is coupled to the bone augment.

With reference to FIG. 34, implant components, such as the articulating member 102 can be directly connected to the bone augment 250, thus making the base plate 350 unnecessary. For example, the stem 106 can directly connect to the coupling surface 258 with a Morse taper fit between the stem 106 of the articulating member 102 and the coupling surface 258 of the bone augment 250.

The bone augments and adapters described herein can be provided as a set or kit. For example, the kit can include one or more of the bone augments 10, 150, 250, 270, 290, and 320, as well as one or more of the adapters 50, 180, or 250. The bone augments 10, 150, 250, 270, 290, and 320 can have various standardized sizes and shapes. Alternatively and as described above, the bone augments 10, 150, 250, 270, 290, and 320 can be patient-specific. The adapters 50, 180, and 250 can be provided in standardized sizes, such as small, medium, and large, to permit coupling with the particular bone augments 10, 150, 250, 270, 290, and 320 included with the kit.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A glenoid prosthesis comprising:
a bone augment comprising:
a substantially cylindrical bone engaging portion having a first end, a second end, and an inner coupling surface that extends from the first end to the second end, the coupling surface defining a tapered adapter recess, the bone engaging portion configured to directly engage a glenoid, and
a flange including an inner surface and an outer surface, the inner surface of the flange located adjacent to an outer surface of the bone engaging portion, the flange outwardly flaring from the inner surface of the flange to the outer surface of the flange;
an adapter having a base at a first end, a tapered stem at a second end, and a tapered intermediate portion in between the base and the tapered stem, the tapered stem configured to connect to the bone augment via the tapered adapter recess, the adapter including an inner surface that defines a tapered receptacle extending through the tapered stem from the first end of the adapter to the second end of the adapter, the flange encircling the bone engaging portion and the base of the adapter at least 180 degrees when implanted; and
an articulating member having a stem receivable within the receptacle and an articulating surface, the articulating surface being concave or convex,
wherein the bone engaging portion and the adapter each have a circular cross-sectional shape and the flange has a semicircular cross-sectional shape,
wherein the outer surface of the flange having a length that is greater than a length of the inner surface of the flange,
wherein the flange further comprises a porous coating and a bone-engaging surface.

2. The glenoid prosthesis of claim 1, wherein the inner coupling surface of the bone engaging portion tapers from the first end of the bone engaging portion to the second end of the bone engaging portion.

3. The glenoid prosthesis of claim 1, wherein the inner coupling surface of the bone engaging portion and the tapered stem of the adapter define a Morse taper connection.

4. The glenoid prosthesis of claim 1, wherein the inner coupling surface of the bone engaging portion includes a first threaded surface and the tapered stem of the adapter includes a second threaded surface configured to engage the first threaded surface.

5. The glenoid prosthesis of claim 1, wherein the flange is integral with the bone engaging portion.

6. The glenoid prosthesis of claim 1, wherein one or more surfaces of the bone augment and the adapter include a porous coating.

* * * * *